(12) United States Patent
Pavlakis et al.

(10) Patent No.: US 6,174,666 B1
(45) Date of Patent: Jan. 16, 2001

(54) METHOD OF ELIMINATING INHIBITORY/ INSTABILITY REGIONS FROM MRNA

(75) Inventors: George N. Pavlakis; Barbara K. Felber, both of Rockville, MD (US)

(73) Assignee: The United States of America as represented by the Department of Health and Human Services, Washington, DC (US)

( * ) Notice: Under 35 U.S.C. 154(b), the term of this patent shall be extended for 0 days.

(21) Appl. No.: 07/858,747

(22) Filed: Mar. 27, 1992

(51) Int. Cl.$^7$ ................................. C12Q 1/70; C12Q 1/68
(52) U.S. Cl. ........................................ 435/5; 435/6
(58) Field of Search ............................ 435/6, 5, 91, 69.1; 935/77

(56) References Cited

FOREIGN PATENT DOCUMENTS

WO9011902    10/1990   (WO) .

OTHER PUBLICATIONS

Kunkel PNAS 82:488–492 (1985).*
Schwartz et al., "Mutational Inactivation of an Inhibitory Sequence in HIV–1 Results in Rev–independent Gag Expression", *Journal of Virology*, vol. 66, 12:7176–7182 (1992) (Not prior art: published after filing date of 07/858, 747 application.).
Copy of Search Report.

* cited by examiner

*Primary Examiner*—Eggerton A. Campbell
(74) *Attorney, Agent, or Firm*—Morgan & Finnegan, L.L.P.

(57) ABSTRACT

A method of locating an inhibitory/instability sequence or sequences within the coding region of an mRNA and modifying the gene encoding that mRNA to remove these inhibitory/instability sequences by making clustered nucleotide substitutions without altering the coding capacity of the gene is disclosed. Constructs containing these mutated genes and host cells containing these constructs are also disclosed. The method and constructs are exemplified by the mutation of a Human Immunodeficiency Virus-1 Rev-dependent gag gene to a Rev-independent gag gene. Constructs useful in locating inhibitory/instability sequences within either the coding region or the 3' untranslated region of an mRNA are also disclosed.

11 Claims, 6 Drawing Sheets

Figure 1C:
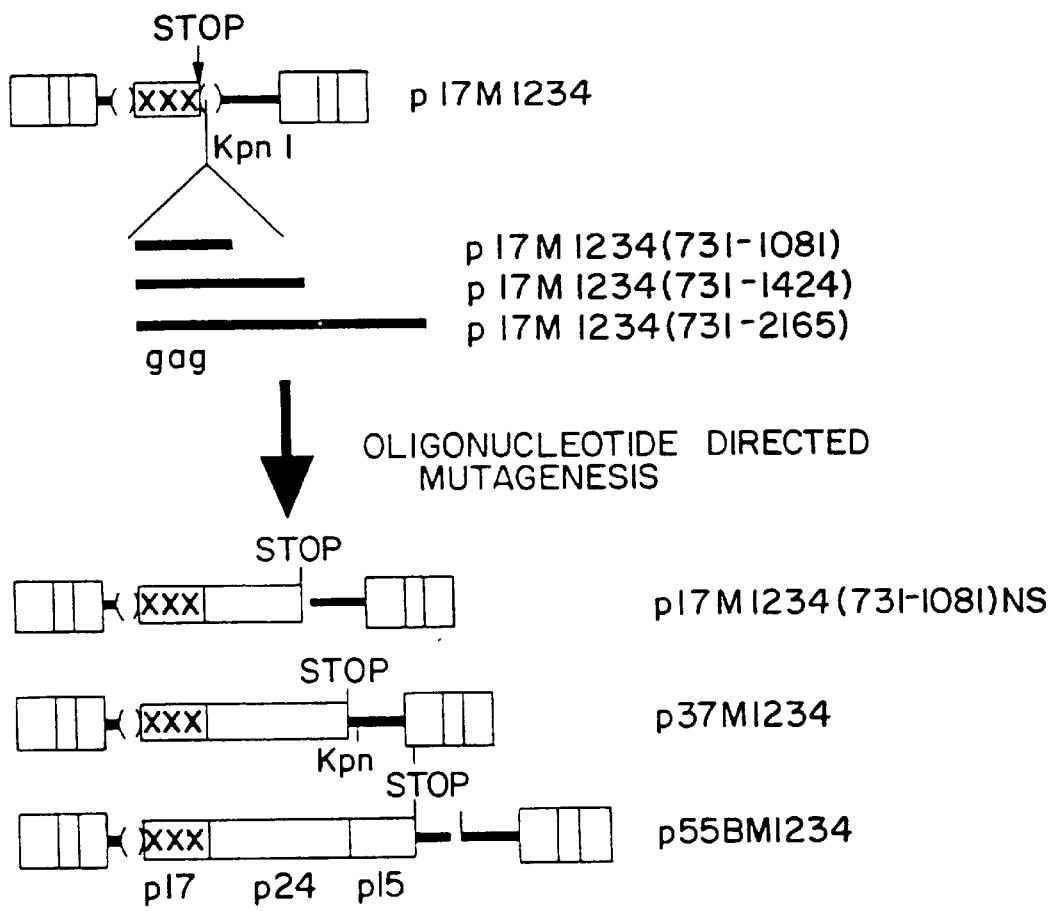

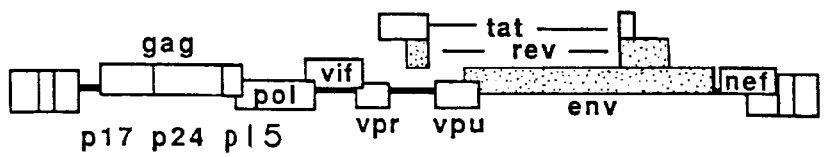
FIG. 1A
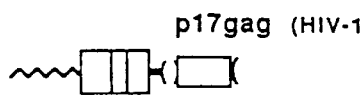 
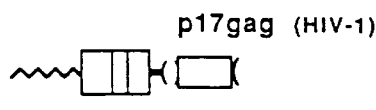 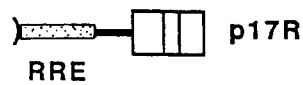
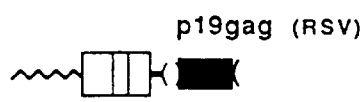 
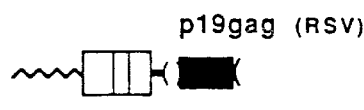 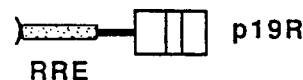
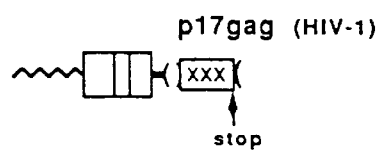 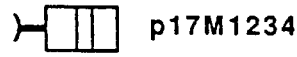
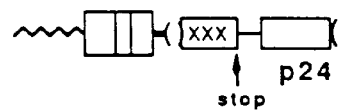 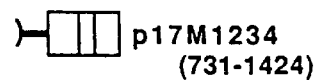
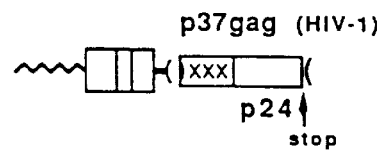 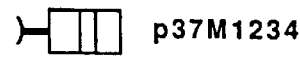
FIG. 1B

```
336
atg ggt gcg aga gcg tca gta tta agc ggg gga gaa tta gat cga tgg gaa aaa att cgg
                                          M1
396
tta agg cca ggg gga aag aaa aaa aaa tat aaa tta aaa cat ata gta tgg gca agc agg gag
              G   G   G   C   G   C   C               C   C
456
cta gaa cga ttc gca gtt aat cct ggc ctg tta gaa aca tca gaa ggc tgt aga caa ata
                                                                  M2
516
ctg gga cag cta caa cca tcc ctt cag aca gga tca gaa gaa ctt aga tca tta tat aat
                              G   G   G   C           C   C   C   C
576
aca gta gca acc ctc tat tgt gtg cat caa agg ata gag ata aaa gac acc aag gaa gct
                          C   G   C           C       G
                              M3                                  M4
636
tta gac aag ata gag gaa gag caa aac aaa agt aag aaa aaa gca cag caa gca gca gct
                              G TCC               G   G   C       G
696
gac aca gga cac agc aat cag gtc agc caa aat tac
```

FIG. 4

METHOD OF ELIMINATING INHIBITORY/INSTABILITY REGIONS FROM MRNA

I. TECHNICAL FIELD

The invention relates to methods of increasing the stability and/or utilization of a mRNA produced by a gene by mutating regulatory or inhibitory/instability sequences (INS) in the coding region of the gene which prevent or reduce expression. The invention also relates to constructs, including expression vectors, containing genes mutated in accordance with these methods and host cells containing these constructs.

The methods of the invention are particularly useful for increasing the stability and/or utilization of a mRNA without changing its protein coding capacity. These methods are useful for allowing or increasing the expression of genes which would otherwise not be expressed or which would be poorly expressed because of the presence of INS regions in the mRNA transcript. Thus, the methods, constructs and host cells of the invention are useful for increasing the amount of protein produced by any gene which encodes an mRNA transcript which contains an INS.

The methods of the invention are useful for increasing the amount of protein produced from genes such as those coding for growth hormones, interferons, interleukins, the fos proto-oncogene protein, and HIV-1 gag and env, for example.

The invention also relates to certain exemplified constructs which can be used to simply and rapidly detect and/or define the boundaries of inhibitory/instability sequences in any mRNA, methods of using these constructs, and host cells containing these constructs. Once the INS regions of the mRNAs have been located and/or further defined, the nucleotide sequences encoding these INS regions can be mutated in accordance with the method of this invention to allow the increase in stability and/or utilization of the mRNA and, therefore, allow an increase in the amount of protein produced from expression vectors encoding the mutated mRNA.

II. BACKGROUND ART

While much work has been devoted to studying transcriptional regulatory mechanisms, it has become increasingly clear that post-transcriptional processes also modulate the amount and utilization of RNA produced from a given gene. These post-transcriptional processes include nuclear post-transcriptional processes (e.g., splicing, polyadenylation, and transport) as well as cytoplasmic RNA degradation. All these processes contribute to the final steady-state level of a particular transcript. These points of regulation create a more flexible regulatory system than any one process could produce alone. For example, a short-lived message is less abundant than a stable one, even if it is highly transcribed and efficiently processed. The efficient rate of synthesis ensures that the message reaches the cytoplasm and is translated, but the rapid rate of degradation guarantees that the mRNA does not accumulate to too high a level. Many RNAs, for example the mRNAS for proto-oncogenes c-myc and c-fos, have been studied which exhibit this kind of regulation in that they are expressed at very low levels, decay rapidly and are modulated quickly and transiently under different conditions. See, M. Hentze, Biochim. Biophys. Acta 1090:281–292 (1991) for a review. The rate of degradation of many of these mRNAs has been shown to be a function of the presence of one or more instability/inhibitory sequences within the mRNA itself.

Some cellular genes which encode unstable or short-lived mRNAs have been shown to contain A and U-rich (AU-rich) INS within the 3' untranslated region (3' UTR) of the transcript mRNA. These cellular genes include the genes encoding granulocyte-monocyte colony stimulating factor (GM-CSF), whose AU-rich 3'UTR sequences (containing 8 copies of the sequence motif AUUUA) are more highly conserved between mice and humans than the protein encoding sequences themselves (93% versus 65%) (G. Shaw, and R. Kamen, Cell 46:659–667 (1986)) and the myc proto-oncogene (c-myc), whose untranslated regions are conserved throughout evolution (for example, 81% for man and mouse) (M. Cole and S. E. Mango, Enzyme 44:167–180 (1990)). Other unstable or short-lived mRNAs which have been shown to contain AU-rich sequences within the 3' UTR include interferons (alpha, beta and gamma IFNs); interleukins (IL1, IL2 and IL3); tumor necrosis factor (TNF); lymphotoxin (Lym); IgG1 induction factor (IgG IF); granulocyte colony stimulating factor (G-CSF), myb proto-oncogene (c-myb); and sis proto-oncogene (c-sis) (G. Shaw, and R. Kamen, Cell 46:659–667 (1986)). See also, R. Wisdom and W. Lee, Gen. & Devel. 5:232–243 (1991) (c-myc); A. Shyu et al., Gen. & Devel. 5:221–231 (1991) (c-fos); T. Wilson and R. Treisman, Nature 336:396–399 (1988) (c-fos); T. Jones and M. Cole, Mol. Cell Biol. 7:4513–4521 (1987) (c-myc); V. Kruys et al., Proc. Natl. Acad. Sci. USA. 89:673–677 (1992) (TNF); D. Koeller et al., Proc. Natl. Acad. Sci. USA. 88:7778–7782 (1991) (transferrin receptor (TfR) and c-fos); I. Laird-Offringa et al., Nucleic Acids Res. 19:2387–2394 (1991) (c-myc); D. Wreschner and G. Rechavi, Eur. J. Biochem. 172:333–340 (1988) (which contains a survey of genes and relative stabilities); Bunnell et al., Somatic Cell and Mol. Genet. 16:151–162 (1990) (galactosyltransferase-associated protein (GTA), which contains an AU-rich 3' UTR with regions that are 98% similar among humans, mice and rats); and Caput et al. Proc. Natl. Acad. Sci. 83:1670–1674 (1986) (TNF, which contains a 33 nt AU-rich sequence conserved in toto in the murine and human TNF mRNAs).

Some of these cellular genes which have been shown to contain INS within the 3' UTR of their mRNA have also been shown to contain INS within the coding region. See, e.g., R. Wisdom, and W. Lee, Gen. & Devel. 5:232–243 (1991) (c-myc); A. Shyu et al., Gen. & Devel. 5:221–231 (1991) (c-fos).

Like the cellular mRNAs, a number of HIV-1 mRNAs have also been shown to contain INS within the protein coding regions, which in some cases coincide with areas of high AU-content. For example, a 218 nucleotide region with high AU content (61.5%) present in the HIV-1 gag coding sequence and located at the 5' end of the gag gene has been implicated in the inhibition of gag expression. S. Schwartz et al., J. Virol. 66:150–159 (1992). Further experiments have indicated the presence of more than one INS in the gag-protease gene region of the viral genome (see below). Regions of high AU content have been found in the HIV-1 gag/pol and env INS regions. The AUUUA sequence is not present in the gag coding sequence, but it is present in many copies within gag/pol and env coding regions. S. Schwartz et al., J. Virol. 66:150–159 (1992). See also, e.g., M. Emerman, Cell 57:1155–1165 (1989) (env gene contains both 3' UTR and internal inhibitory/instability sequences); C. Rosen, Proc. Natl. Acad. Sci., USA 85:2071–2075 (1988) (env); M. Hadzopoulou-Cladaras et al., J. Virol. 63:1265–1274 (1989) (env); F. Maldarelli et al., J. Virol. 65:5732–5743 (1991) (gag/pol); A. Cochrane et al., J. Virol. 65:5303–5313 (1991) (pol). F. Maldarelli et al., supra, note that the direct analysis of the function of INS regions in the context of a replication-competent, full-length HIV-1 provirus is complicated by the fact that the intragenic INS are located in the coding sequences of virion structural proteins. They further note that changes in these intragenic INS sequences would in most cases affect protein sequences as well, which in turn could affect the replication of such mutants.

The INS regions are not necessarily AU-rich. For example, the c-fos coding region INS is structurally unrelated to the AU-rich 3' UTR INS (A. Shyu et al., Gen. & Devel. 5:221–231 (1991), and the env coding region, which appears to contain INS elements, is not AU-rich. Furthermore, some stable transcripts also carry the AUUUA motif in their 3' UTRs, implying either that this sequence alone is not sufficient to destabilize a transcript, or that these messages also contain a dominant stabilizing element (M. Cole and S. E. Mango, Enzyme 44:167–180 (1990)). Interestingly, elements unique to specific mRNAs have also been found which can stabilize a mRNA transcript. One example is the Rev responsive element, which in the presence of Rev protein promotes the transport, stability and utilization of a mRNA transcript (B. Felber et al., Proc. Natl. Acad. Sci. USA 86:1495–1499 (1989)).

It is not yet known whether the AU sequences themselves, and specifically the Shaw-Kamen sequence, AUUUA, act as part or all of the degradation signal. Nor is it clear whether this is the only mechanism employed for short-lived messages, or if there are different classes of RNAs, each with its own degradative system. See, M. Cole and S. E. Mango, Enzyme 44:167–180 (1990) for a review; see also, T. Jones and M. Cole, Mol. Cell. Biol. 7:4513–4521 (1987). Mutation of the only copy of the AUUUA sequence in the c-myc RNA INS region has no effect on RNA turnover, therefore the inhibitory sequence may be quite different from that of GM-CSF (M. Cole and S. E. Mango, Enzyme 44:167–180 (1990)), or else the mRNA instability may be due to the presence of additional INS regions within the mRNA.

Previous workers have made mutations in genes encoding AU-rich inhibitory/instability sequences within the 3' UTR of their transcript mRNAs. For example, G. Shaw and R. Kamen, Cell 46:659–667 (1986), introduced a 51 nucleotide AT-rich sequence from GM-CSF into the 3' UTR of the rabbit β-globin gene. This insertion caused the otherwise stable β-globin mRNA to become highly unstable in vivo, resulting in a dramatic decrease in expression of β-globin as compared to the wild-type control. The introduction of another sequence of the same length, but with 14 G's and C's interspersed among the sequence, into the same site of the 3' UTR of the rabbit β-globin gene resulted in accumulation levels which were similar to that of wild-type β-globin mRNA. This control sequence did not contain the motif AUUUA, which occurs seven times in the AU-rich sequence. The results suggested that the presence of the AU-rich sequence in the β-globin mRNA specifically confers instability.

A. Shyu et al., Gen. & Devel. 5:221–231 (1991), studied the AU-rich INS in the 3' UTR of c-fos by disrupting all three AUUUA pentanucleotides by single U-to-A point mutations to preserve the AU-richness of the element while altering its sequence. This change in the sequence of the 3' UTR INS dramatically inhibited the ability of the mutated 3' UTR to destabilize the β-globin message when inserted into the 3' UTR of a β-globin mRNA as compared to the wild-type INS. The c-fos protein-coding region INS (which is structurally unrelated to the 3' UTR INS) was studied by inserting it in-frame into the coding region of a β-globin and observing the effect of deletions on the stability of the heterologous c-fos-β-globin mRNA.

Previous workers have also made mutations in genes encoding inhibitory/instability sequences within the coding region of their transcript mRNAs. For example, P. Carter-Muenchau and R. Wolf, Proc. Natl. Acad. Sci., USA, 86:1138–1142 (1989) demonstrated the presence of a negative control region that lies deep in the coding sequence of the E. coli 6-phosphogluconate dehydrogenase (gnd) gene. The boundaries of the element were defined by the cloning of a synthetic "internal complementary sequence" (ICS) and observing the effect of this internal complementary element on gene expression when placed at several sites within the gnd gene. The effect of single and double mutations introduced into the synthetic ICS element by site-directed mutagenesis on regulation of expression of a gnd-lacz fusion gene correlated with the ability of the respective mRNAs to fold into secondary structures that sequester the ribosome binding site. Thus, the gnd gene's internal regulatory element appears to function as a cis-acting antisense RNA.

M. Lundigran et al., Proc. Natl. Acad. Sci. USA 88:1479–1483 (1991), conducted an experiment to identify sequences linked to btuB that are important for its proper expression and transcriptional regulation in which a DNA fragment carrying the region from −60 to +253 (the coding region starts at +241) was mutagenized and then fused in frame to lacZ. Expression of β-galactosidase from variant plasmids containing a single base change were then analyzed. The mutations were all GC to AT transitions, as expected from the mutagenesis procedures used. Among other mutations, a single base substitution at +253 resulted in greatly increased expression of the btuB-lacZ gene fusion under both repressing and nonrepressing conditions.

R. Wisdom and W. Lee, Gen. & Devel. 5:232–243 (1991), conducted an experiment which showed that mRNA derived from a hybrid full length c-myc gene, which contains a mutation in the translation initiation codon from ATG to ATC, is relatively stable, implying that the c-myc coding region inhibitory sequence functions in a translation dependent manner.

R. Parker and A. Jacobson, Proc. Natl. Acad. Sci. USA 87:2780–2784 (1990) demonstrated that a region of 42 nucleotides found in the coding region of Saccharomyces cerevisiae MATα1 mRNA, which normally confers low stability, can be experimentally inactivated by introduction of a translation stop codon immediately upstream of this 42 nucleotide segment. The experiments suggest that the decay of MATα1 mRNA is promoted by the translocation of ribosomes through a specific region of the coding sequence. This 42 nucleotide segment has a high content (8 out of 14) of rare codons (where a rare codon is defined by its occurrence fewer than 13 times per 1000 yeast codons (citing S. Aota et al., Nucl. Acids. Res. 16:r315–r402 (1988))) that may induce slowing of translation elongation. The authors of the study, R. Parker and A. Jacobson, state that the concentration of rare codons in the sequences required for rapid decay, coupled with the prevalence of rare codons in unstable yeast mRNAs and the known ability of rare codons to induce translational pausing, suggests a model in which mRNA structural changes may be affected by the particular positioning of a paused ribosome. Another author stated that it would be revealing to find out whether (and how) a kinetic change in translation elongation could affect mRNA stability (M. Hentze, Bioch. Biophys. Acta 1090:281–292 (1991))). R. Parker and A. Jacobson, note, however, that the stable PGK1 mRNA can be altered to include up to 40% rare codons with, at most, a 3-fold effect on steady-state mRNA level and that this difference may actually be due to a change in transcription rates. Thus, these authors conclude, it seems unlikely that ribosome pausing per se is sufficient to promote rapid mRNA decay.

None of the aforementioned references describe or suggest the present invention of locating inhibitory/instability sequences within the coding region of an mRNA and modifying the gene encoding that mRNA to remove these inhibitory/instability sequences by making multiple nucleotide substitutions without altering the coding capacity of the gene.

III. DISCLOSURE OF THE INVENTION

The invention relates to methods of increasing the stability and/or utilization of a mRNA produced by a gene by mutating regulatory or inhibitory/instability sequences (INS) in the coding region of the gene which prevent or reduce expression. The invention also relates to constructs, including expression vectors, containing genes mutated in accordance with these methods and host cells containing these constructs.

As defined herein, an inhibitory/instability sequence of a transcript is a regulatory sequence that resides within an mRNA transcript and is either (1) responsible for rapid turnover of that mRNA and can destabilize a second indicator/reporter mRNA when fused to that indicator/reporter mRNA, or is (2) responsible for underutilization of a mRNA and can cause decreased protein production from a second indicator/reporter mRNA when fused to that second indicator/reporter mRNA or (3) both of the above. The inhibitory/instability sequence of a gene is the gene sequence that encodes an inhibitory/instability sequence of a transcript. As used herein, utilization refers to the overall efficiency of translation of an mRNA.

The methods of the invention are particularly useful for increasing the stability and/or utilization of a mRNA without changing its protein coding capacity. However, alternative embodiments of the invention in which the inhibitory/instability sequence is mutated in such a way that the amino acid sequence of the encoded protein is changed to include conservative or non-conservative amino acid substitutions, while still retaining the function of the originally encoded protein, are also envisioned as part of the invention.

These methods are useful for allowing or increasing the expression of genes which would otherwise not be expressed or which would be poorly expressed because of the presence of INS regions in the mRNA transcript. The invention provides methods of increasing the production of a protein encoded by a gene which encodes an mRNA containing an inhibitory/instability region by altering the portion of the nucleotide sequence of any gene encoding the inhibitory/instability region.

The methods, constructs and host cells of the invention are useful for increasing the amount of protein produced by any gene which encodes an mRNA transcript which contains an INS. Examples of such genes include, for example, those coding for growth hormones, interferons, interleukins, and the fos proto-oncogene protein, as well as the genes coding for HIV-1 gag and env proteins.

The method of the invention is exemplified by the mutational inactivation of an INS within the coding region of the HIV-1 gag gene which results in increased gag expression, and by constructs useful for Rev-independent gag expression in human cells. This mutational inactivation of the inhibitory/instability sequences involves introducing multiple point mutations into the AU-rich inhibitory sequences within the coding region of the gag gene which, due to the degeneracy of nucleotide coding sequences, do not affect the amino acid sequence of the gag protein.

The constructs of the invention are exemplified by vectors containing the gag and env genes which have been mutated in accordance with the methods of this invention and the host cells are exemplified by human HLtat cells containing these vectors.

The invention also relates to certain exemplified constructs which can be used to simply and rapidly detect and/or further define the boundaries of inhibitory/instability sequences in any mRNA which is known or suspected to contain such regions, whether the INS are within the coding region or in the 3'UTR or both. Once the INS regions of the genes have been located and/or further defined through the use of these vectors, the same vectors can be used in mutagenesis experiments to eliminate the identified INS without affecting the coding capacity of the gene, thereby allowing an increase in the amount of protein produced from expression vectors containing these mutated genes. The invention also relates to methods of using these constructs and to host cells containing these constructs.

The constructs of the invention which can be used to detect instability/inhibitory regions within an mRNA are exemplified by the vectors, p19, p17M1234 and p37M1234, which are set forth in FIG. 1. (B). p37M1234 is the preferred construct, due to the existence of a commercially available ELISA test which allows the simple and rapid detection of any changes in the amount of expression of the gag indicator/reporter protein. However, any constructs which contain the elements depicted between the long terminal repeats in the aforementioned constructs of FIG. 1. (B), and which can be used to detect instability/inhibitory regions within a mRNA, are also envisioned as part of this invention.

The existence of inhibitory/instability sequences has been known in the art, but no solution to the problem which allowed increased expression of the genes encoding the mRNAs containing these sequences by making multiple nucleotide substitutions, without altering the coding capacity of the gene, has heretofore been disclosed.

IV. BRIEF DESCRIPTION OF THE DRAWINGS

FIG. 1. (A) Structure of the HIV-1 genome. Boxes indicate the different viral genes. (B) Structure of the gag expression plasmids (see infra). Plasmid p17 contains the complete HIV-1 5' LTR and sequences up to the BssHII restriction site at nucleotide (nt) 257. (The nucleotide numbering refers to the revised nucleotide sequence of the HIV-1 molecular clone pHXB2 (G. Myers et al., Eds. *Human retroviruses and AIDS. A compilation and analysis of nucleic acid and amino acid sequences* (Los Alamos National Laboratory, Los Alamos, N.Mex., 1991), incorporated herein by reference). This sequence is followed by the p17$^{gag}$ coding sequence spanning nt 336–731 (represented as an open box) immediately followed by a translational stop codon and a linker sequence. Adjacent to the linker is the HIV-1 3' LTR from nt 8561 to the last nucleotide of the U5 region. Plasmid p17R contains in addition the 330 nt StyI fragment encompassing the RRE (L. Solomin et al., J Virol 64:6010–6017 (1990)) (represented as a stippled box) 3' to the p17$^{gag}$ coding sequence. The RRE is followed by HIV-1 sequences from nt 8021 to the last nucleotide of the U5 region of the 3' LTR. Plasmids p19 and p19R were generated by replacing the HIV-1 p17$^{gag}$ coding sequence in plasmids p17 and p17R, respectively, with the RSV p19$^{gag}$ coding sequence (represented as a black box). Plasmid p17M1234 is identical to p17, except for the presence of 28 silent nucleotide substitutions within the gag coding region, indicated by XXX. Wavy lines represent plasmid sequences. Plasmid p17M1234(731–1424) and plasmid p37M1234 are described immediately below and in the description. These vectors are illustrative of constructs which can be used to determine whether a particular nucleotide sequence encodes an INS. In this instance, vector p17M1234, which contains an indicator gene (here, p17$^{gag}$) represents the control vector and vectors p17M1234(731–1424) and p37M1234 represent vectors in which the nucleotide sequence of interest (here the p24$^{gag}$ coding region) is inserted into the vector either 3' to the stop codon of the indicator gene or is fused in frame to the coding region of the indicator gene, respectively. (C) Construction of expression vectors for identification of gag INS and for further mutagenesis. p17M1234 was used as a vector to insert additional HIV-1 gag sequences downstream from the coding region of the altered p17$^{gag}$ gene. Three different fragments indicated by nucleotide numbers were inserted into vector p17M1234 as described below. To generate plasmids p17M1234(731–1081), p17M1234 (731–1424) and p17M1234(731–2165), the indicated fragments were inserted 3' to the stop codon of the p17$^{gag}$ coding sequence in p17M1234. In expression assays (data not shown), p17M1234(731–1081) and p17M1234(731–1424) expressed high levels of p17$^{gag}$ protein. In contrast, p17M1234(731–2165) did not express p17$^{gag}$ protein, indicating the presence of additional INS within the HIV-1 gag coding region. To generate plasmids p17M1234(731–1081) NS, p37M1234 and p55M1234, the stop codon at the end of the altered p17$^{gag}$ gene and all linker sequences in p17M1234 were eliminated by oligonucleotide-directed mutagenesis and the resulting plasmids restored the gag open reading frame as in HIV-1. In expression assays (data not shown) p37M1234 expressed high levels of protein as determined by western blotting and ELISA assays whereas p55M1234 did not express any detectable gag protein. Thus, the addition of sequences 3' to the p24 region resulted in the elimination of protein expression, indicating that nucleotide sequence 1424–2165 contains an INS. This experiment demonstrated that p37M1234 is an appropriate vector to analyze additional INS.

Figure 2A:
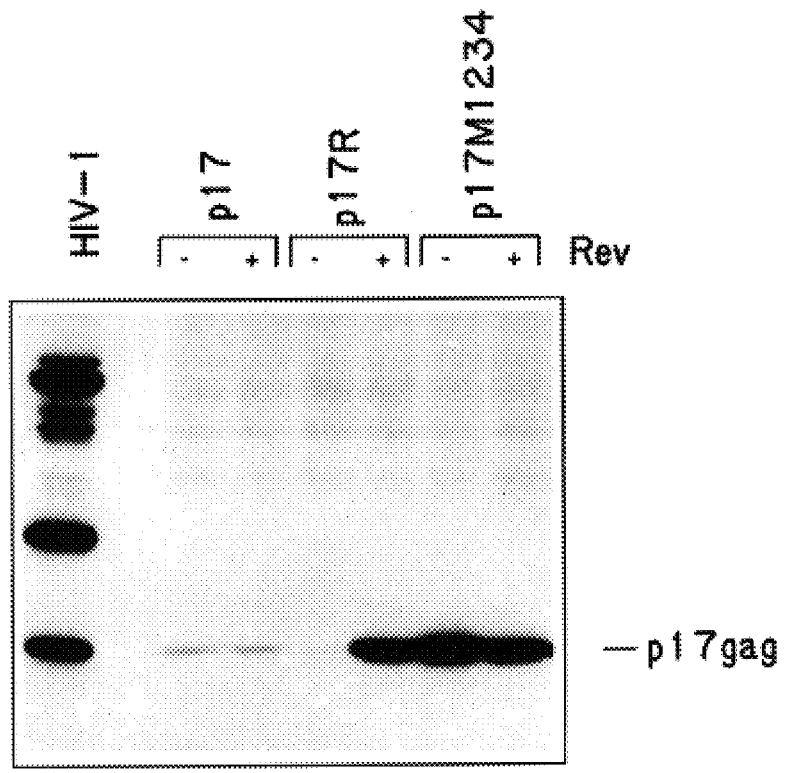
Figure 2B:
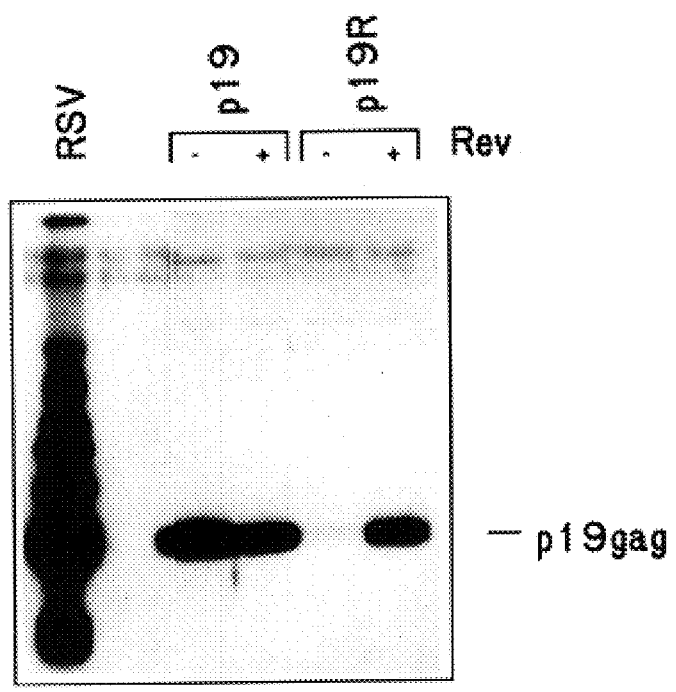

FIG. 2. Gag expression from the different vectors. (A) HLtat cells were transfected with plasmid p17, p17R, or p17M1234 in the absence (−) or presence (+) of Rev (see infra). The transfected cells were analyzed by immunoblotting using a human HIV-1 patient serum. (B) Plasmid p19 or p19R was transfected into HLtat cells in the absence (−) or presence (+) of Rev. The transfected cells were analyzed by immunoblotting using rabbit and anti-RSV p19$^{gag}$ serum. HIV or RSV proteins served as markers in the same gels. The positions of p17$^{gag}$ and p19$^{gag}$ are indicated at right.

FIG. 3. mRNA analysis on northern blots (A) HLtat cells were transfected with the indicated plasmids in the absence (−) or presence (+) of Rev. 20 μg of total RNA prepared from the transfected cells were analyzed (see infra). (B) RNA production from plasmid p19 or p19R was similarly analyzed in the absence (−) or presence (+) of Rev.

FIG. 4. Nucleotide sequence of the HIV-1 p17$^{gag}$ region. The locations of the 4 oligonucleotides (M1–M4) used to generate all mutants are underlined. The silent nucleotide substitutions introduced by each mutagenesis oligonucleotide are indicated below the coding sequence. Numbering starts from nt +1 of the viral mRNA.

Figure 5:
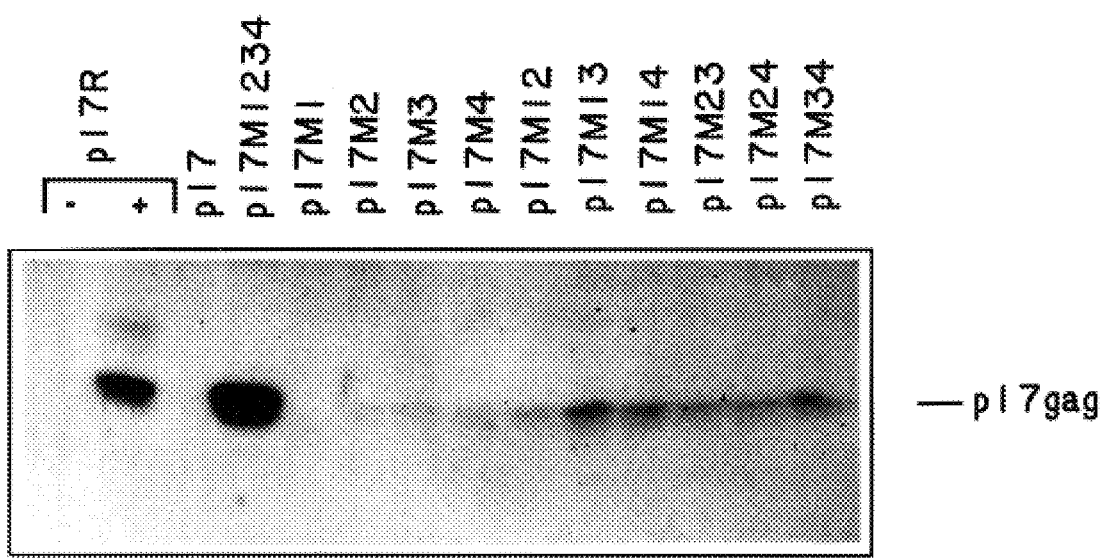

FIG. 5. Gag expression by different mutants. HLtat cells were transfected with the various plasmids indicated at the top of the figure. Plasmid p17R was transfected in the absence (−) or presence (+) of Rev, while the other plasmids were analyzed in the absence of Rev. p17$^{gag}$ production was assayed by immunoblotting as described in FIG. 2.

V. MODES FOR CARRYING OUT THE INVENTION

It is to be understood that both the foregoing general description and the following detailed description are exemplary and explanatory only, and are not restrictive of the invention, as claimed. The accompanying drawings, which are incorporated in and constitute a part of the specification, illustrate an embodiment of the invention and, together with the description, serve to explain the principles of the invention.

The invention comprises methods for eliminating intragenic inhibitory/instability regions of an mRNA by (a) identifying the intragenic inhibitory/instability regions, and (b) mutating the intragenic inhibitory/instability regions by making multiple point mutations. These mutations may be clustered. This method does not require the identification of the exact location or knowledge of the mechanism of function of the INS. Generally, the mutations are such that the amino acid sequence encoded by the mRNA is unchanged, although conservative and non-conservative amino acid substitutions are also envisioned as part of the invention where the protein encoded by the mutated gene is substantially similar to the protein encoded by the non-mutated gene.

The nucleotides to be altered can be chosen randomly, the only requirement being that the amino acid sequence encoded by the protein remain unchanged; or, if conservative and non-conservative amino acid substitutions are to be made, the only requirement is that the protein encoded by the mutated gene be substantially similar to the protein encoded by the non-mutated gene.

If the INS region is AT rich or GC rich, it is preferable that it be altered so that it has a content of about 50% G and C and about 50% A and T. If the INS region contains less-preferred codons, it is preferable that those be altered to more-preferred codons. If desired, however (e.g., to make an A and T rich region more G and C rich), more-preferred codons can be altered to less-preferred codons. If the INS region contains conserved nucleotides, some of those conserved nucleotides could be altered to non-conserved nucleotides. Again, the only requirement is that the amino acid sequence encoded by the protein remain unchanged; or, if conservative and non-conservative amino acid substitutions are to be made, the only requirement is that the protein encoded by the mutated gene be substantially similar to the protein encoded by the non-mutated gene.

As used herein, conserved nucleotides means evolutionarily conserved nucleotides for a given gene, since this conservation may reflect the fact that they are part of a signal involved in the inhibitory/instability determination. Conserved nucleotides can generally be determined from published references about the gene of interest or can be determined by using a variety of computer programs available to practitioners of the art.

Less-preferred and more-preferred codons for various organisms can be determined from codon usage charts, such as those set forth in T. Maruyama et al., Nucl. Acids Res. 14:r151–r197 (1986) and in S. Aota et al., Nucl. Acids. Res. 16:r315–r402 (1988), or through use of a computer program, such as that disclosed in U.S. Pat. No. 5,082,767 entitled "Codon Pair Utilization", issued to G. W. Hatfield et al. on Jan. 21, 1992, which is incorporated herein by reference.

Generally, the method of the invention is carried out as follows:

1. Identification of an mRNA containing an INS

The rate at which a particular protein is made is usually proportional to the cytoplasmic level of the mRNA which encodes it. Thus, a candidate for an mRNA containing an inhibitory/instability sequence is one whose mRNA or protein is either not detectably expressed or is expressed poorly as compared to the level of expression of a reference mRNA or protein under the control of the same or similar strength promoter. Differences in the steady state levels of a particular mRNA (as determined, for example, by Northern blotting), when compared to the steady state level of mRNA from another gene under the control of the same or similar strength promoter, which cannot be accounted for by changes in the apparent rate of transcription (as determined, for example, by nuclear run-on assays) indicate that the gene is a candidate for an unstable mRNA. In addition or as an alternative to being unstable, cytoplasmic mRNAs may be poorly utilized due to various inhibitory mechanisms acting in the cytoplasm. These effects may be mediated by specific mRNA sequences which are named herein as "inhibitory sequences".

Candidate mRNAs containing inhibitory/instability regions include mRNAs from genes whose expression is tightly regulated, e.g., many oncogenes, growth factor genes and genes for biological response modifiers such as interleukins. Many of these genes are expressed at very low levels, decay rapidly and are modulated quickly and transiently under different conditions. The negative regulation of expression at the level of mRNA stability and utilization has been documented in several cases and has been proposed to be occurring in many other cases. Examples of genes for which there is evidence for post-transcriptional regulation due to the presence of inhibitory/instability regions in the mRNA include the cellular genes encoding granulocyte-monocyte colony stimulating factor (GM-CSF), proto-oncogenes c-myc, c-myb, c-sis, c-fos; interferons (alpha, beta and gamma IFNs); interleukins (IL1, IL2 and IL3); tumor necrosis factor (TNF); lymphotoxin (Lym); IgG1 induction factor (IgG IF); granulocyte colony stimulating factor (G-CSF); transferrin receptor (TfR); and galactosyltransferase-associated protein (GTA); HIV-1 genes encoding env, gag and pol; the E. coli genes for 6-phosphogluconate dehydrogenase (gnd) and btuB; and the yeast gene for MATα1 (see the discussion in the "Background Art" section, above). The genes encoding the cellular proto-oncogenes c-myc and c-fos, as well as the yeast gene for MATα1 and the HIV-1 genes for gag, env and pol are genes for which there is evidence for inhibitory/instability regions within the coding region in addition to evidence for inhibitory/instability regions within the non-coding region. Genes encoding or suspected of encoding mRNAs containing inhibitory/instability regions within the coding region are particularly relevant to the invention.

After identifying a candidate unstable or poorly utilized mRNA, the in vivo half-life (or stability) of that mRNA can be studied by conducting pulse-chase experiments (i.e., labeling newly synthesized RNAs with a radioactive precursor and monitoring the decay of the radiolabeled mRNA in the absence of label); or by introducing in vitro transcribed mRNA into target cells (either by microinjection, calcium phosphate co-precipitation, electroporation, or other methods known in the art) to monitor the in vivo half-life of the defined mRNA population; or by expressing the mRNA under study from a promoter which can be induced and which shuts off transcription soon after induction, and estimating the half-life of the mRNA which was synthesized during this short transcriptional burst; or by blocking transcription pharmacologically (e.g., with Actinomycin D) and following the decay of the particular mRNA at various time points after the addition of the drug by Northern blotting or RNA protection (e.g. S1 nuclease) assays. Methods for all the above determinations are well established. See, e.g., Hentze et al., Biochim. Biophys. Acta 1090:281–292 (1991) and references cited therein. See also, S. Schwartz et al., J. Virol. 66:150–159 (1992). The most useful measurement is how much protein is produced, because this includes all possible INS mechanisms. Examples of various mRNAs which have been shown to contain or which are suspected to contain INS regions are described above. Some of these mRNAs have been shown to have half-lives of less than 30 minutes when their mRNA levels are measured by Northern blots (see, e.g., D. Wreschner and G. Rechavi, Eur. J. Biochem. 172:333–340 (1988)).

2. Localization of Instability Determinants

When an unstable or poorly utilized mRNA has been identified, the next step is to search for the responsible (cis-acting) RNA sequence elements. Detailed methods for localizing the cis-acting inhibitory/instability regions are set forth in each of the references described in the "Background Art" section, above, and are also discussed infra. The exemplified constructs of the present invention can also be used to localize INS (see below). Cis acting sequences responsible for specific mRNA turnover can be identified by deletion and point mutagenesis as well as by the occasional identification of naturally occurring mutants with an altered mRNA stability.

In short, to evaluate whether putative regulatory sequences are sufficient to confer mRNA stability control, DNA sequences coding for the suspected INS regions are fused to an indicator (or reporter) gene to create a gene coding for a hybrid mRNA. The DNA sequences fused to the indicator (or reporter) gene can be cDNA, genomic DNA or synthesized DNA. Examples of indicator (or reporter) genes that are described in the references set forth in the "Background Art" section include the genes for neomycin, β-galactosidase, chloramphenicol acetetyltransferase (CAT), and luciferase, as well as the genes for β-globin, PGK1 and ACT1. See also Sambrook et al., Molecular Cloning, A Laboratory Manual, 2d. ed. Cold Spring Harbor Laboratory, Cold Spring Harbor, N.Y., (1989), pp. 16.56–16.67. Other genes which can be used as indicator genes are disclosed herein (i.e., the gag gene of the Rous Sarcoma Virus (which lacks an inhibitory/instability region) and the Rev independent HIV-1 gag genes of constructs p17M1234 and p37M1234, which have been mutated to inactivate the inhibitory/instability region and which constitute one aspect of the invention. In general, virtually any gene encoding a mRNA which is stable or which is expressed at relatively high levels (defined here as being stable enough or expressed at high enough level so that any decrease in the level of the mRNA or expressed protein can be detected by standard methods) can be used as an indicator or reporter gene, although the construct p37M1234, which is exemplified herein, is preferred for reasons set forth below. Preferred methods of creating hybrid genes using these constructs and testing the expression of mRNA and protein from these constructs are also set forth below.

In general, the stability and/or utilization of the mRNAs generated by the indicator gene and the hybrid genes consisting of the indicator gene fused to the sequences suspected of encoding an INS region are tested by transfecting the hybrid genes into host cells which are appropriate for the expression vector used to clone and express the mRNAs. The resulting levels of mRNA are determined by standard methods of determining mRNA stability, e.g. Northern blots, S1 mapping or PCR methods, and the resulting levels of protein produced are quantitated by protein measuring assays, such as ELISA, immunoprecipitation and/or western blots. The inhibitory/instability region (or regions, if there are more than one) will be identified by a decrease in the protein expression and/or stability of the hybrid mRNA as compared to the control indicator mRNA. Note that if the ultimate goal is to increase production of the encoded protein, the identification of the INS is most preferably carried out in the same host cell as will be used for the production of the protein.

Examples of some of the host cells that have been used to detect INS sequences include somatic mammalian cells, Xenopus oocytes, yeast and E. coli. See, e.g., G. Shaw and R. Kamen, Cell 46:659–667 (1986) (discussed supra) which localized inhibitory/instability sequences in GM-CSF by inserting putative inhibitory sequences into the 3' UTR of the β-globin gene, causing the otherwise stable β-globin mRNA to become unstable when transfected into mouse or human cells. See also I. Laird-Offringa et al., Nucleic Acids Res. 19:2387–2394 (1991) which localized inhibitory/instability sequences in c-myc using hybrid c-myc-neomycin resistance genes introduced into rat fibroblasts, and M. Lundigran et al., Proc. Natl. Acad. Sci. USA 88:1479–1483 (1991) which localized inhibitory/instability sequences in btuB gene by using hybrid btuB-lacZ genes introduced into E. coli. For examples of localization of specific inhibitory/instability sequences within a transcript of HIV-1 by destabilization of an otherwise long-lived indicator transcript, see, e.g., M. Emerman, Cell 57:1155–1165 (1989) (replaced 3' UTR of env gene with part of HBV and introduced into COS-1 cells); S. Schwartz et al., J. Virol. 66:150–159 (1992) (gag gene fusions with Rev independent tat reporter gene introduced into HeLa cells); F. Maldarelli et al., J. Virol. 65:5732–5743 (1991) (gag/pol gene fusions with Rev independent tat reporter gene or chloramphenicol acetyltransferase (CAT) gene introduced into HeLa and SW480 cells); and A. Cochrane et al., J. Virol. 65:5303–5313 (1991) (pol gene fusions with CAT gene or rat proinsulin gene introduced into COS-1 and CHO cells).

It is anticipated that in vitro mRNA degradation systems (e.g., crude cytoplasmic extracts) to assay mRNA turnover in vitro will complement ongoing in vivo analyses and help to circumvent some of the limitations of the in vivo systems. See Hentze et al., Biochim. Biophys. Acta 1090:281–292 (1991) and references cited therein. See also D. Wreschner and G. Rechavi, Eur. J. Biochem. 172:333–340 (1988), which analyzed exogenous mRNA stability in a reticulocyte lysate cell-free system.

In the method of the invention, the whole gene of interest may be fused to an indicator or reporter gene and tested for its effect on the resulting hybrid mRNA in order to determine whether that gene contains an inhibitory/instability region or regions. To further localize the INS within the gene of interest, fragments of the gene of interest may be prepared by sequentially deleting sequences from the gene of interest from either the 5' or 3' ends or both. The gene of interest may also be separated into overlapping fragments by methods known in the art (e.g., with restriction endonucleases, etc.) See, e.g., S. Schwartz et al., J. Virol. 66:150–159 (1992). Preferably, the gene is separated into overlapping fragments about 300 to 2000 nucleotides in length. Two types of vector constructs can be made. To permit the detection of inhibitory/instability regions that do not need to be translated in order to function, vectors can be constructed in which the gene of interest (or its fragments or suspected INS) can be inserted into the 3' UTR downstream from the stop codon of an indicator or reporter gene. This does not permit translation through the INS. To test the possibility that some inhibitory/instability sequences may act only after translation of the mRNA, vectors can be constructed in which the gene of interest (or its fragments or suspected INS) is inserted into the coding region of the indicator/reporter gene. This method will permit the detection of inhibitory/instability regions that do need to be translated in order to function. The hybrid constructs are transfected into host cells, and the resulting mRNA levels are determined by standard methods of determining mRNA stability, e.g. Northern blots, S1 mapping or PCR methods, as set forth above and as described in most of the references cited in the "Background Art" section. See also, Sambrook et al. (1989), supra, for experimental methods. The protein produced from such genes is also easily quantitated by existing assays, such as ELISAS, immunoprecipitation and western blots, which are also described in most of the references cited in the "Background Art" section. See also, Sambrook et al. (1989), supra, for experimental methods. The hybrid DNAs containing the inhibitory/instability region (or regions, if there are more than one) will be identified by a decrease in the protein expression and/or stability of the hybrid mRNA as compared to the control indicator mRNA. The use of various fragments of the gene permits the identification of multiple independently functional inhibitory/instability regions, if any, while the use of overlapping fragments lessen the possibility that an inhibitory/instability region will not be identified as a result of its being cut in half, for example.

The exemplified test vectors set forth in FIG. 1. (B) and described herein, e.g., vectors p17M1234, p37M1234 and, p19, can be used to assay for the presence and location of INS in various RNAs, including INS which are located within coding regions. These vectors can also be used to determine whether a gene of interest not yet characterized has INS which are candidates for mutagenesis curing. These vectors have a particular advantage over the prior art in that the same vectors can be used in the mutagenesis step of the invention (described below) in which the identified INS is eliminated without affecting the coding capacity of the gene.

The method of using these vectors involves introducing the entire gene, entire cDNA or fragments of the gene ranging from approximately 300 nucleotides to approximately 2 kilobases 3' to the coding region for gag protein using unique restriction sites which are engineered into the vectors. The expression of the gag gene in HLtat cells is measured at both the RNA and protein levels, and compared to the expression of the starting vectors. A decrease in expression indicates the presence of INS candidates that may be cured by mutagenesis. The method of using the vectors exemplified in FIG. 1 herein involves introducing the entire gene and fragments of the gene of interest into vectors p17M1234, p37M1234 and p19. The size of the fragments are preferably 300–2000 nucleotides long. Plasmid DNA is prepared in E. coli and purified by the CsCl method.

To permit detection of inhibitory/instability regions which do not need to be translated in order to function, the entire gene and fragments of the gene of interest are introduced into vectors p17M1234, p37M1234 or p19 3' of the stop codon of the p17$^{gag}$ coding region. To allow the detection of inhibitory/instability regions that affect expression only when translated, the described vectors can be manipulated so that the coding region of the entire gene or fragments of the gene of interest are fused in frame to the expressed gag protein gene. For example, a fragment containing all or part of the coding region of the gene of interest can be inserted exactly 3' to the termination codon of the gag coding sequence in vector p37M1234 and the termination codon of gag and the linker sequences can be removed by oligonucleotide mutagenesis in such a way as to fuse the gag reading frame to the reading frame of the gene of interest.

RNA and protein production from the two expression vectors (e.g. p37M1234 containing the fragment of the gene of interest inserted directly 3' of the stop codon of the gag coding region, with the gag termination codon intact, and p37M1234 containing the fragment of the gene of interest inserted in frame with the gag coding region, with the gag termination codon deleted) are then compared after transfection of purified DNA into HLtat cells.

The expression of these vectors after transfection into human cells is monitored at both the level of RNA and protein production. RNA levels are quantitated by, e.g., Northern blots, S1 mapping or PCR methods. Protein levels are quantitated by, e.g., western blot or ELISA methods. p37M1234 is ideal for quantitative analysis because a fast non-radioactive ELISA protocol can be used to detect gag protein (DUPONT or COULTER gag antigen capture assay). A decrease in the level of expression of the gag antigen indicates the presence of inhibitory/instability regions within the cloned gene or fragment of the gene of interest.

After the inhibitory/instability regions have been identified, the vectors containing the appropriate INS fragments can be used to prepare single-stranded DNA and then used in mutagenesis experiments with specific chemically synthesized oligonucleotides in the clustered mutagenesis protocol described below.

3. Mutation of the Inhibitory/Instability Regions to Generate Stable mRNAs

Once the inhibitory/instability sequences are located within the coding region of an mRNA, the gene is modified to remove these inhibitory/instability sequences without altering the coding capacity of the gene. Alternatively, the gene is modified to remove the inhibitory/instability sequences, simultaneously altering the coding capacity of the gene to encode either conservative or non-conservative amino acid substitutions.

In the method of the invention, the most general method of eliminating the INS in the coding region of the gene of interest is by making multiple mutations in the INS region of the gene or gene fragments, without changing the amino acid sequence of the protein encoded by the gene; or, if conservative and non-conservative amino acid substitutions are to be made, the only requirement is that the protein encoded by the mutated gene be substantially similar to the protein encoded by the non-mutated gene. It is preferred that all of the suspected inhibitory/instability regions, if more than one, be mutated at once. Later, if desired, each inhibitory/instability region can be mutated separately in order to determine the smallest region of the gene that needs to be mutated in order to generate a stable mRNA. The ability to mutagenize long DNA regions at the same time can decrease the time and effort needed to produce the desired stable and/or highly expressed mRNA and resulting protein. The altered gene or gene fragments containing these mutations will then be tested in the usual manner, as described above, e.g., by fusing the altered gene or gene fragment with a reporter or indicator gene and analyzing the level of mRNA and protein produced by the altered genes after transfection into an appropriate host cell. If the level of mRNA and protein produced by the hybrid gene containing the altered gene or gene fragment is about the same as that produced by the control construct encoding only the indicator gene, then the inhibitory/instability regions have been effectively eliminated from the gene or gene fragment due to the alterations made in the INS.

In the method of the invention, more than two point mutations will be made in the INS region. Optionally, point mutations may be made in at least about 10% of the nucleotides in the inhibitory/instability region. These point mutations may also be clustered. The nucleotides to be altered can be chosen randomly (i.e., not chosen because of AT or GC content or the presence or absence of rare or preferred codons), the only requirement being that the amino acid sequence encoded by the protein remain unchanged; or, if conservative and non-conservative amino acid substitutions are to be made, the only requirement is that the protein encoded by the mutated gene be substantially similar to the protein encoded by the non-mutated gene.

In the method of the present invention, the gene sequence can be mutated so that the encoded protein remains the same due to the fact that the genetic code is degenerate, i.e., many of the amino acids may be encoded by more than one codon. The base code for serine, for example, is six-way degenerate such that the codons TCT, TCG, TCC, TCA, AGT, and AGC all code for serine. Similarly, threonine is encoded by any one of codons ACT, ACA, ACC and ACG. Thus, a plurality of different DNA sequences can be used to code for a particular set of amino acids. The codons encoding the other amino acids are TTT and TTC for phenylalanine; TTA, TTG, CTT, CTC, CTA amd CTG for leucine; ATT, ATC and ATA for isoleucine; ATG for methione; GTT, GTC, GTA and GTG for valine; CCT, CCC, CCA and CCG for proline; GCU, GCC, GCA and GCG for alanine; TAT and TAC for tyrosine; CAT and CAC for histidine; CAA and CAG for glutamine; AAT and AAC for asparagine; AAA and AAG for lysine; GAT and GAC for aspartic acid; GAA and GAG for glutamic acid; TGT and TGC for cysteine; TGG for tryptophan; CGT, CGC, CGA and CGG for arginine; and GGU, GGC, GGA and GGG for glycine. Charts depicting the codons (i.e., the genetic code) can be found in various general biology or biochemistry textbooks.

In the method of the present invention, if the portion(s) of the gene encoding the inhibitory/instability regions are AT-rich, it is preferred, but not believed to be necessary, that most or all of the mutations in the inhibitory/instability region be the replacement of A and T with G and C nucleotides, making the regions more GC-rich, while still maintaining the coding capacity of the gene. If the portion(s) of the gene encoding the inhibitory/instability regions are GC-rich, it is preferred, but not believed to be necessary, that most or all of the mutations in the inhibitory/instability region be the replacement of G and C nucleotides with A and T nucleotides, making the regions less GC-rich, while still maintaining the coding capacity of the gene. If the INS region is either AT-rich or GC-rich, it is most preferred that it be altered so that it has a content of about 50% G and C and about 50% A and T. The AT- (or AU-) content (or, alternatively, the GC-content) of an inhibitory/instability region or regions can be calculated by using a computer program designed to make such calculations. Such programs, used to determine the AT-richness of the HIV-1 gag inhibitory/instability regions exemplified herein, are the GCG Analysis Package for the VAX (University of Wisconsin) and the Gene Works Package (Intelligenetics).

In the method of the invention, if the INS region contains less-preferred codons, it is preferable that those be altered to more-preferred codons. If desired, however (e.g., to make an AT-rich region more GC-rich), more-preferred codons can be altered to less-preferred codons. It is also preferred, but not believed to be necessary, that less-preferred or rarely used codons be replaced with more-preferred codons. Optionally, only the most rarely used codons (identified from published codon usage tables, such as in T. Maruyama et al., Nucl. Acids Res. 14(Supp):r151–197 (1986)) can be replaced with preferred codons, or alternatively, most or all of the rare codons can be replaced with preferred codons. Generally, the choice of preferred codons to use will depend on the codon usage of the host cell in which the altered gene is to be expressed. Note, however, that the substitution of more-preferred codons with less-preferred codons is also functional, as shown in the example below.

As noted above, coding sequences are chosen on the basis of the genetic code and, preferably on the preferred codon usage in the host cell or organism in which the mutated gene of this invention is to be expressed. In a number of cases the preferred codon usage of a particular host or expression system can be ascertained from available references (see, e.g., T. Maruyama et al., Nucl. Acids Res. 14(Supp): r151–197 (1986)), or can be ascertained by other methods (see, e.g., U.S. Pat. No. 5,082,767 entitled "Codon Pair Utilization", issued to G. W. Hatfield et al. on Jan. 21, 1992, which is incorporated herein by reference). Preferably, sequences will be chosen to optimize transcription and translation as well as mRNA stability so as to ultimately increase the amount of protein produced. Selection of codons is thus, for example, guided by the preferred use of codons by the host cell and/or the need to provide for desired restriction endonuclease sites and could also be guided by a desire to avoid potential secondary structure constraints in the encoded mRNA transcript. Potential secondary structure constraints can be identified by the use of computer programs such as the one described in M. Zucker et al., Nucl. Acids Res. 9:133 (1981). More than one coding sequence may be chosen in situations where the codon preference is unknown or ambiguous for optimum codon usage in the chosen host cell or organism. However, any correct set of codons would encode the desired protein, even if translated with less than optimum efficiency.

In the method of the invention, if the INS region contains conserved nucleotides, it is also preferred, but not believed to be necessary, that conserved nucleotides sequences in the inhibitory/instability region be mutated. Optionally, at least approximately 75% of the mutations made in the inhibitory/instability region may involve the mutation of conserved nucleotides. Conserved nucleotides can be determined by using a variety of computer programs available to practitioners of the art.

In the method of the invention, it is also anticipated that inhibitory/instability sequences can be mutated such that the encoded amino acids are changed to contain one or more conservative or non-conservative amino acids yet still provide for a functionally equivalent protein. For example, one or more amino acid residues within the sequence can be substituted by another amino acid of a similar polarity which acts as a functional equivalent, resulting in a neutral substitution in the amino acid sequence. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In the exemplified method of the present invention, all of the regions in the HIV-1 gag gene suspected to have inhibitory/instability activity were first mutated at once over a region approximately 270 nucleotides in length using clustered site-directed mutagenesis with four different oligonucleotides spanning a region of approximately 300 nucleotides to generate the construct p17M1234, described infra, which encodes a stable mRNA.

The four oligonucleotides, which are depicted in FIG. 4, are M1: ccaggggaaagaagaagta- caagctaaagcacatcgtatgggcaagcagg (SEQ ID NO.: 6); M2: ccttcagacaggatcagaggagcttcgatcactatacaacacagtagc (SEQ ID NO.: 7); M3: accctctattgtgtgcaccagcgatc- gagatcaaggacaccaaggaagc (SEQ ID NO.: 8); and M4: gag- caaaacaagtccaagaagaaggcccagcaggcagcagctgacacagg (SEQ ID NO.: 9). These oligonucleotides are 51 (M1), 48 (M2), 50 (M3) and 50 (M4) nucleotides in length. Each oligonucleotide introduced several point mutations over an area of 19–22 nucleotides (see infra). The number of nucleotides 5' to the first mutated nucleotide were 14 (M1); 18 (M2); 17 (M3); and 11 (M4); and the number of nucleotides 3' to the last mutated nucleotide were 15 (M1); 8 (M2); 14 (M3); and 17 (M4). The ratios of AT to GC nucleotides present in each of these regions before mutation was 33AT/18GC (M1); 30AT/18GC (M2); 29AT/21GC (M3) and 27AT/23GC (M4). The ratios of AT to GC nucleotides present in each of these regions after mutation was 25AT/26GC (M1); 24AT/24GC (M2); 23AT/27GC (M3,) and 22AT/28GC (M4). A total of 26 codons were changed. The number of times the codon appears in human genes per 1000 codons (from T. Maruyama et al., Nuc. Acids Res. 14 (Supp.):r151–r197 (1986)) is listed in parentheses next to the codon. In the example, 8 codons encoding lysine (Lys) were changed from aaa (22.0) to aag (35.8); two codons encoding tyrosine (Tyr) were changed from tat (12.4) to tac (18.4); two codons encoding leucine (Leu) were changed from tta (5.9) to cta (6.1); two codons encoding histidine (His) were changed from cat (9.8) to cac (14.3); three codons encoding isoleucine (Ile) were changed from ata (5.1) to atc (24.0); two codons encoding glutamic acid (Glu) were changed from gaa (26.8) to gag (41.6); one codon encoding arginine (Arg) was changed from aga (10.8) to cga (5.2) and one codon encoding arginine (Arg) was changed from agg (11.4) to cgg (7.7); one codon encoding asparagine (Asn) was changed from aat (16.9) to aac (23.6); two codons encoding glutamine (Gln) were changed from caa (11.5) to cag (32.7); one codon encoding serine (Ser) was changed from agt (8.7) to tcc (18.7); and one codon encoding alanine (Ala) was changed from gca (12.7) to gcc (29.8).

The techniques of oligonucleotide-directed site-specific mutagenesis employed to effect the modifications in structure or sequence of the DNA molecule are known to those of skill in the art. The target DNA sequences which are to be mutagenized can be cDNA, genomic DNA or synthesized DNA sequences. Generally, these DNA sequences are cloned into an appropriate vector, e.g., a bacteriophage M13 vector, and single-stranded template DNA is prepared from a plaque generated by the recombinant bacteriophage. The single-stranded DNA is annealed to the synthetic oligonucleotides and the mutagenesis and subsequent steps are performed by methods well known in the art. See, e.g., M. Smith and S. Gillam, in *Genetic Engineering: Principles* and Methods, Plenum Press 3:1–32 (1981) (review) and T. Kunkel, Proc. Natl. Acad. Sci. USA 82:488–492 (1985). See also, Sambrook et al. (1989), supra. The synthetic oligonucleotides can be synthesized on a DNA synthesizer (e.g., Applied Biosystems) and purified by electrophoresis by methods known in the art. The length of the selected or prepared oligodeoxynucleotides using this method can vary. There are no absolute size limits. As a matter of convenience, for use in the process of this invention, the shortest length of the oligodeoxynucleotide is generally approximately 20 nucleotides and the longest length is generally approximately 60 to 100 nucleotides. The size of the oligonucleotide primers are determined by the requirement for stable hybridization of the primers to the regions of the gene in which the mutations are to be induced, and by the limitations of the currently available methods for synthesizing oligonucleotides. The factors to be considered in designing oligonucleotides for use in oligonucleotide-directed mutagenesis (e.g., overall size, size of portions flanking the mutation(s)) are described by M. Smith and S. Gillam in Genetic Engineering: Principles and Methods, Plenum Press 3:1–32 (1981). In general, the overall length of the oligonucleotide will be such as to optimize stable, unique hybridization at the mutation site with the 5' and 3' extensions from the mutation site being of sufficient size to avoid editing of the mutationss) by the exonuclease activity of the DNA polymerase. Oligonucleotides used for mutagenesis in the present invention will generally be at least about 20 nucleotides, usually about 40 to 60 nucleotides in length and usually will not exceed about 100 nucleotides in length. The oligonucleotides will usually contain at least about five bases 3' of the altered codons.

In the preferred mutagenesis protocol of the present invention, the INS containing expression vectors contain the BLUESCRIPT plasmid vector as a backbone. This enables the preparation of double-stranded as well as single-stranded DNA. Single-stranded uracil containing DNA is prepared according to a standard protocol as follows: The plasmid is transformed into a F' bacterial strain (e.g. DH5aF'). A colony is grown and infected with the helper phage M13-VCS [Stratagene #20025; 1×10$^{11}$ pfu/ml]. This phage is used to infect a culture of the E. coli strain CJ236 and single-stranded DNA is isolated according to standard methods. 0.25 ug of single-stranded DNA is annealed with the synthesized oligonucleotides (5 ul of each oligo, dissolved at a concentration of 5 OD$_{260}$/ml. The synthesized oligonucleotides are usually about 40 to 60 nucleotides in length and are designed to contain a perfect match of approximately 10 nucleotides at each end. They may contain as many changes as desired within the remaining 20–40 nucleotides. The oligonucleotides are designed to cover the region of interest and they may be next to each other or there may be gaps between them. Up to six different oligonucleotides have been used at the same time, although it is believed that the use of more than six oligonucleotides at the same time would also work in the method of this invention. After annealing, elongation with T4 polymerase produces the second strand which does not contain uracil. The free ends are ligated using ligase. This results in double-stranded DNA which can be used to transform E. coli strain HB101. The mutated strand which does not contain uracil produces double-stranded DNA, which contains the introduced mutations. Individual colonies are picked and the mutations are quickly verified by sequence analysis. Alternatively or additionally/ this mutagenesis method can (and has been) used to select for different combinations of oligonucleotides which result in different mutant phenotypes. This facilitates the analysis of the regions important for function and is helpful in subsequent experiments because it allows the analysis of exact sequences involved in the INS. In addition to the exemplified mutagenesis of the INS-1 region of HIV-1 described herein, this method has also been used to mutate in one step a region of 150 nucleotides using three tandemly arranged oligonucleotides that introduced a total of 35 mutations. The upper limit of changes is not clear, but it is estimated that regions of approximately 500 nucleotides can be changed in 20% of their nucleotides in one step using this protocol.

The exemplified method of mutating by using oligonucleotide-directed site-specific mutagenesis may be varied by using equivalent methods known in the art. For example, the mutated gene can be synthesized directly using overlapping synthetic deoxynucleotides (see, e.g., Edge et al. Nature 292:756 (1981); Nambair et al., Science 223:1299 (1984); Jay et al., J. Biol. Chem. 259:6311 (1984); or by using a combination of polymerase chain reaction generated DNAs or cDNAs and synthesized oligonucleotides.

4. Determination of Stability of the Mutated mRNA

The steady state level and/or stability of the resultant mutated mRNAs can be tested in the same manner as the steady state level and/or stability of the unmodified mRNA containing the inhibitory/instability regions are tested (e.g., by Northern blotting), as discussed in section 1, above. The mutated mRNA can be analyzed along with (and thus compared to) the unmodified mRNA containing the inhibitory/instability region(s) and with an unmodified indicator mRNA, if desired. As exemplified, the HIV-1 p17$^{gag}$ mutants are compared to the unmutated HIV-1 p17$^{gag}$ in transfection experiments by subsequent analysis of the mRNAs by Northern blot analysis. The proteins produced by these mRNAs are measured by immunoblotting and other methods known in the art, such as ELISA. See infra.

VI. INDUSTRIAL APPLICABILITY

Genes which can be mutated by the methods of this invention include those whose mRNAs are known or suspected of containing INS regions in their mRNAs. These genes include, for example, those coding for growth hormones, interferons, interleukins, the fos proto-oncogene protein, and HIV-1 gag and env, as well as other viral mRNAs in addition to those exemplified herein. Genes mutated by the methods of this invention can be expressed in the native host cell or organism or in a different cell or organism. The mutated genes can be introduced into a vector such as a plasmid, cosmid, phage, virus or mini-chromosome and inserted into a host cell or organism by methods well known in the art. In general, the mutated genes or constructs containing these mutated genes can be utilized in any cell, either eukaryotic or prokaryotic, including mammalian cells (e.g., human (e.g., HeLa), monkey (e.g., Cos), rabbit (e.g., rabbit reticulocytes), rat, hamster (e.g., CHO and baby hamster kidney cells) or mouse cells (e.g., L cells), plant cells, yeast cells, insect cells or bacterial cells (e.g., E. coli). The vectors which can be utilized to clone and/or express these mutated genes are the vectors which are capable of replicating and/or expressing the mutated genes in the host cell in which the mutated genes are desired to be replicated and/or expressed. See, e.g., F. Ausubel et al., Current Protocols in Molecular Biology, Greene Publishing Associates and Wiley-Interscience (1992) and Sambrook et al. (1989) for examples of appropriate vectors for various types of host cells. The native promoters for such genes can be replaced with strong promoters compatible with the host into which the gene is inserted. These promoters may be inducible. The host cells containing these mutated genes can be used to express large amounts of the protein useful in enzyme preparations, pharmaceuticals, diagnostic reagents, vaccines and therapeutics.

The proteins made by using constructs encoding the exemplified altered gag and env genes could be used, for example, in the production of diagnostic reagents, vaccines and therapies for AIDS and AIDS related diseases. The inhibitory/instability elements in the exemplified HIV-1 gag gene may be involved in the establishment of a state of low virus production in the host. HIV-1 and the other lentiviruses cause chronic active infections that are not cleared by the immune system. It is possible that complete removal of the inhibitory/instability sequence elements from the lentiviral genome would result in constitutive expression. This could prevent the virus from establishing a latent infection and escaping immune system surveillance. The success in increasing expression of p17$^{gag}$ by eliminating the inhibitory sequence element suggests that one could produce lentiviruses without any negative elements. Such lentiviruses could provide a novel approach towards attenuated vaccines. Identification of similar inhibitory/instability elements in SIV indicates that this virus may provide a convenient model to test this hypothesis.

The exemplified constructs can be used to simply and rapidly detect and/or further define the boundaries of inhibitory/instability sequences in any mRNA which is known or suspected to contain such regions, e.g., in mRNAs encoding various growth hormones, interferons or interleukins, as well as other viral mRNAs in addition to those exemplified herein.

The following examples illustrate certain embodiments of the present invention, but should not be construed as limiting its scope in any way. Certain modifications and variations will be apparent to those skilled in the art from the teachings of the foregoing disclosure and the following examples, and these are intended to be encompassed by the spirit and scope of the invention.

EXAMPLE 1

HIV-1 GAG GENE

The interaction of the Rev regulatory protein of human immunodeficiency virus type 1 (HIV-1) with its RNA target, named the Rev-responsive element (RRE), is necessary for expression of the viral structure proteins (for reviews see G. Pavlakis and B. Felber, New Biol. 2:20–31 (1990); B. Cullen and W. Greene, Cell 58:423–426 (1989); and C. Rosen and G. Pavlakis, AIDS J. 4:499–509 (1990)). Rev acts by promoting the nuclear export and increasing the stability of the RRE-containing mRNAs. Recent results also indicate a role for REV in the efficient polysome association of these mRNAs (S. Arrigo and I. Chen, Gene Dev. 5:808–819 (1991), D. D'Agostino et al., Mol. Cell Biol. 12:1375–1386 (1992)). Since the RRE-containing HIV-1 mRNAs do not efficiently produce protein in the absence of Rev, it has been postulated that these mRNAs are defective and contain inhibitory/instability sequences variously designated as INS, CRS, or IR (M. Emerman et al. Cell 57:1155–1165 (1989); S. Schwartz et al., J. Virol. 66:150–159 (1992); C. Rosen et al., Proc. Natl. Acad. Sci. USA 85:2071–2075 (1988); M. Hadzopoulou-Cladaras et al., J. Virol. 63:1265–1274 (1989); F. Maldarelli et al., J. Virol. 65:5732–5743 (1991); A. W. Cochrane et al., J. Virol. 65:5305–5313 (1991)). The nature and function of these inhibitory/instability sequences have not been characterized in detail. It has been postulated that inefficiently used splice sites may be necessary for Rev function (D. Chang and P. Sharp, Cell 59:789–795 (1989)); the presence of such splice sites may confer Rev-dependence to HIV-1 mRNAs.

Analysis of HIV-1 hybrid constructs led to the initial characterization of some inhibitory/instability sequences in the gag and pol regions of HIV-1 (S. Schwartz et al., J. Virol. 66:150–159 (1992); F. Maldarelli et al., J Virol 65:5732–5743 (1991); A. W. Cochrane et al., J. Virol. 65:5305–5313 (1991)). The identification of an inhibitory/instability RNA element located in the coding region of the p17$^{gag}$ matrix protein of HIV-1 was also reported (S. Schwartz et al., J. Virol. 66:150–159 (1992)). It was shown that this sequence acted in cis to inhibit HIV-1 tat expression after insertion into a tat cDNA. The inhibition could be overcome by Rev-RRE, demonstrating that this element plays a role in regulation by Rev. To further study the inhibitory/instability element in p17$^{gag}$, a p17$^{gag}$ expression plasmid (p17, FIG. 1) was constructed. The p17$^{gag}$ sequence was engineered to contain a translational stop codon immediately after the coding sequence and thus could produce only p17$^{gag}$ (the construction of this plasmid is described below). The major 5' splice site of HIV-1 upstream of the gag AUG has been deleted from this vector (B. Felber et al., Proc. Natl. Acad. Sci. USA 86:1495–1499 (1989)). To investigate whether plasipid p17 could produce p17$^{gag}$ in the absence of Rev and the RRE, p17 was transfected into HLtat cells (S. Schwartz et al., J. Virol. 64:2519–2529 (1990)) (see below). These cells constitutively produce HIV-1 Tat protein, which is necessary for transactivation of the HIV-1 LTR promoter. Plasmid p17 was transfected in the absence or presence of Rev, and the production of p17$^{gag}$ was analyzed by western immunoblotting. The results revealed that very low levels of p17$^{gag}$ protein were produced (FIG. 2A). The presence of Rev did not increase gag expression, as expected, since this mRNA did not contain the RRE. Next, a plasmid that contained both the p17$^{gag}$ coding sequence and the RRE (p17R, FIG. 1) was constructed. Like p17, this plasmid produced very low levels of p17$^{gag}$ in the absence of Rev. High levels of p17$^{gag}$ were produced only in the presence of Rev (FIG. 2A). These experiments suggested that an inhibitory/instability element was located in the p17$^{gag}$ coding sequence.

Expression experiments using various eucaryotic vectors have indicated that several other retroviruses do not contain such inhibitory/instability sequences within their coding sequences (see for example, J. Wills et al., J. Virol. 63:4331–43 (1989) and V. Morris et al., J. Virol. 62:349–53 (1988)). To verify these results, the p17$^{gag}$ (matrix) gene of HIV-1 in plasmid p17 was replaced with the coding sequence for p19$^{gag}$ (matrix) which is the homologous protein of the Rous sarcoma virus (RSV, strain SR-A). The resulting plasmid, p19 (FIG. 1), was identical to plasmid p17, except for the gag coding sequence. The production of p19$^{gag}$ protein from plasmid p19 was analyzed by western immunoblotting, which revealed that this plasmid produced high levels of p19$^{gag}$ (FIG. 2A). These experiments demonstrated that the p19$^{gag}$ coding sequence of RSV, in contrast to p17$^{gag}$ of HIV-1, could be efficiently expressed in this vector, indicating that the gag region of RSV did not contain any inhibitory/instability elements. A derivative of plasmid p19 that contained the RRE, named p19R (FIG. 1) was also constructed. Interestingly, only very low levels of p19$^{gag}$ protein were produced from the RRE-containing plasmid p19R in the absence of Rev. This observation indicated that the introduced RRE and 3' HIV-1 sequences exerted an inhibitory effect on p19$^{gag}$ expression from plasmid p19R, which is in agreement with recent data indicating that in the absence of Rev, a longer region at the 3' end of the virus including the RRE acts as an inhibitory/instability element (G. Nasioulas, G. Pavlakis, B. Felber, manuscript in preparation). In conclusion, the high levels of expression of RSV p19$^{gag}$ in the same vector reinforced the conclusion that an inhibitory/instability sequence within HIV-1 p17$^{gag}$ coding region was responsible for the very low levels of expression.

Figure 3A:
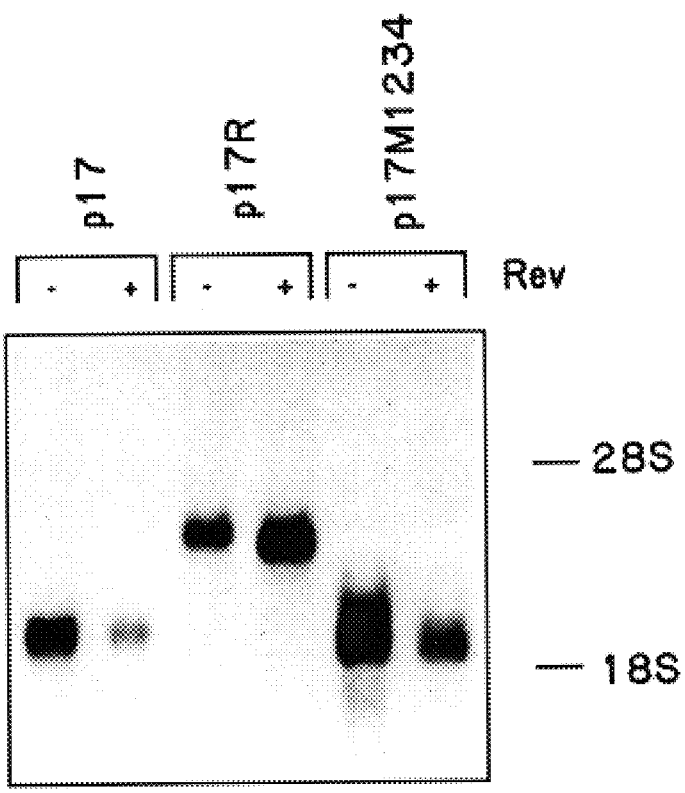
Figure 3B:
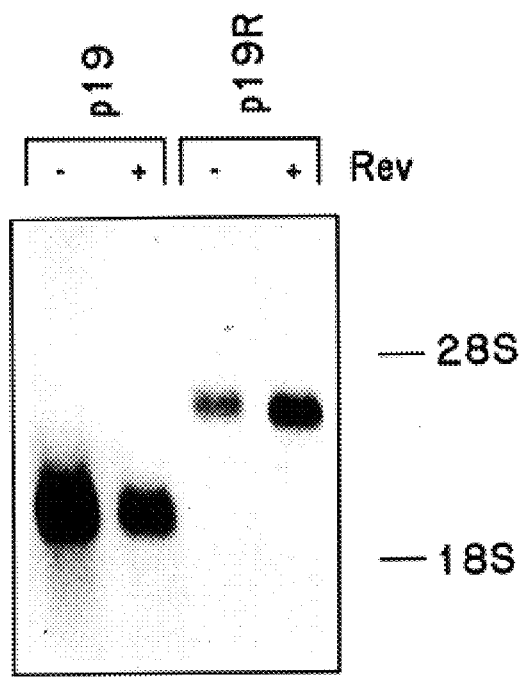

It was next determined whether the inhibitory/instability effect of the p17$^{gag}$ coding sequence was detected also at the mRNA level. Northern blot analysis of RNA extracted from HLtat cells transfected with p17 or transfected with p17R demonstrated that p17R produced lower mRNA levels in the absence of Rev (FIG. 3A) (See Example 3). A two- to eight-fold increase in p17R mRNA levels was observed after coexpression with Rev. Plasmid p17 produced mRNA levels similar to those produced by p17R in the absence of Rev. Notably, Rev decreased the levels of mRNA and protein produced by mRNAs that do not contain RRE. This inhibitory effect of Rev in cotransfection experiments has been observed for many other non-RRE-containing mRNAs, such as luciferase and CAT (L. Solomin et al., J. Virol 64:6010–6017 (1990); D. M. Benko et al., New Biol 2:1111–1122 (1990)). These results established that the inhibitory element in gag also affects the mRNA levels and are in agreement with previous findings (S. Schwartz et al., J. Virol. 66:150–159 (1992)). Quantitations of the mRNA and protein levels produced by p17R in the absence or presence of Rev were performed by scanning densitometry of appropriate serial dilutions of the samples, and indicated that the difference was greater at the level of protein (60- to 100-fold) than at the level of mRNA (2- to 8-fold). This result is compatible with previous findings of effects of Rev on mRNA localization and polysomal loading of both gag and env mRNAs (S. Arrigo et al., Gene Dev 5:808–819 (1991); D. D'Agostino et al., Mol. Cell. Biol. 12:1375–1386 (1992); M. Emerman et al., Cell 57:1155–1165 (1989); B. Felber et al., Proc. Natl. Acad. Sci. USA 86:1495–1499 (1989), M. Malim et al., Nature (London) 338:254–257 (1989)). Northern blot analysis of the mRNAs produced by the RSV gag expression plasmids revealed that p19 produced high mRNA levels (FIG. 3B). This further demonstrated that the p19$^{gag}$ coding sequence of RSV does not contain inhibitory elements. The presence of the RRE and 3' HIV-1 sequences in plasmid p19R resulted in decreased mRNA levels in the absence of Rev, further suggesting that inhibitory elements were present in these sequences. Taken together, these results established that gag expression in HIV-1 is fundamentally different from that in RSV. The HIV-1 p17$^{gag}$ coding sequence contains a strong inhibitory element while the RSV p19$^{gag}$ coding sequence does not. Interestingly, plasmid p19 contains the 5' splice site used to generate the RSV env mRNA, which is located downstream of the gag AUG. This 5' splice site is not utilized in the described expression vectors (FIG. 3B). Mutation of the invariable GT dinucleotide of this 5' splice site to AT did not affect p19$^{gag}$ expression significantly (data not shown). On the other hand, the HIV-1 p17 expression plasmid did not contain any known splice sites, yet was not expressed in the absence of Rev. These results further indicate that sequences other than inefficiently used splice sites are responsible for inhibition of gag expression.

To investigate the exact nature of the inhibitory element in HIV-1 gag, site-directed mutagenesis of the p17$^{gag}$ coding sequence with four different oligonucleotides, as indicated in FIG. 4, was performed. Each oligonucleotide introduced several point mutations over an area of 19–22 nucleotides. These mutations did not affect the amino acid sequence of the p17$^{gag}$ protein, since they introduced silent codon changes. First, all four oligonucleotides were used simultaneously in mutagenesis using a single-stranded DNA template as described (T. Kunkel, Proc. Natl. Acad. Sci. USA 82:488–492 (1985); S. Schwartz et al., Mol. Cell. Biol. 12:207–219 (1992)). This allowed the simultaneous introduction of many point mutations over a large region of 270 nt in vector p17. A mutant containing all four oligonucleotides was isolated and named p17M1234. Compared to p17, this plasmid contained a total of 28 point mutations distributed primarily in regions with high AU-content. The phenotype of the mutant was assessed by transfections into HLtat cells and subsequent analysis of p17$^{gag}$ expression by immunoblotting. Interestingly, p17M1234 produced high levels of p17$^{gag}$ protein, higher than those produced by p17R in the presence of Rev (FIG. 2A). This result demonstrated that the inhibitory/instability signals in p17$^{gag}$ mRNA had been inactivated in plasmid p17M1234. As expected, the presence of Rev protein did not increase expression from p17M1234, but instead, had a slight inhibitory effect on gag expression. Thus, p17$^{gag}$ expression from the mutant p17M1234 displayed the same general properties as the p19$^{gag}$ of RSV, that is, a high constitutive level of Rev-independent gag expression. Northern blot analysis revealed that the mRNA levels produced by p17M1234 were increased compared to those produced by p17 (FIG. 3A).

To further examine the nature and exact location of the minimal inhibitory/instability element, the p17$^{gag}$ coding sequence in plasmid p17 was mutated with only one of the four mutated oligonucleotides at a time. This procedure resulted in four mutant plasmids, named p17M1, p17M2, p17M3, and p17M4, according to the oligonucleotide that each contains. None of these mutants produced significantly higher levels of p17$^{gag}$ protein compared to plasmid p17 (FIG. 5), indicating that the inhibitory/instability element was not affected. The p17 coding sequence was next mutated with two oligonucleotides at a time. The resulting mutants were named p17M12, p17M13, p17M14, p17M23, p17M24, and p17M34. Protein production from these mutants was minimally increased compared with that from p17, and it was considerably lower than that from p17M1234 (FIG. 5). In addition, a triple oligonucleotide mutant, p17M123, also failed to express high levels of p17$^{gag}$ (data not shown). These findings may suggest that multiple inhibitory/instability signals are present in the coding sequence of p17$^{gag}$. Alternatively, a single inhibitory/instability element may span a large region, whose inactivation requires mutagenesis with more than two oligonucleotides. This possibility is consistent with previous data suggesting that a 218-nucleotide inhibitory/instability element in the p17$^{gag}$ coding sequence is required for strong inhibition of gag expression. Further deletions of this sequence resulted in gradual loss of inhibition (S. Schwartz et al., J. Virol. 66:150–159 (1992)). The inhibitory/instability element may coincide with a specific secondary structure on the mRNA. It is currently being investigated whether a specific structure is important for the function of the inhibitory/instability element.

The p17$^{gag}$ coding sequence has a high content of A and U nucleotides, unlike the coding sequence of p19$^{gag}$ of RSV (S. Schwartz et al., J. Virol. 66:150–159 (1992); G. Myers and G. Pavlakis, in *The Retroviridae* J. Levy, Eds. (Plenum Press, New York, NY, 1991), pp. 1–37). Four regions with high AU content are present in the p17$^{gag}$ coding sequence and have been implicated in the inhibition of gag expression (S. Schwartz et al., J. Virol. 66:150–159 (1992)). Lentiviruses have a high AU content compared to the mammalian genome. Regions of high AU content are found in the gag/pol and env regions, while the multiply spliced mRNAs have a lower AU content (G. Myers and G. Pavlakis, in *The Retroviridae,* J. Levy, Eds. (Plenum Press, New York, N.Y., 1991), pp. 1–37), supporting the possibility that the inhibitory/instability elements are associated with mRNA regions with high AU content. It has been shown that a specific oligonucleotide sequence, AUUUA, found at the AU-rich 3' untranslated regions of some unstable mRNAs, may confer RNA instability (G. Shaw and R. Kamen, Cell 46:659–667 (1986)). Although this sequence is not present in the p17$^{gag}$ sequence, it is found in many copies within gag/pol and env regions. The association of instability elements with AU-rich regions is not universal, since the RRE together with 3' HIV sequences, which shows a strong inhibitory/instability activity in our vectors, is not AU-rich. These observations suggest the presence of more than one type of inhibitory/instability sequences. In addition to reducing the AU content, some of the mutations introduced in plasmid p17 changed rarely used codons to more favored codons for human cells. Although the use of rare codons could be an alternative explanation for poor HIV gag expression, this type of translational regulation is not favored by these results, since the presence of Rev corrects the defect in gag expression. In addition, the observation that the presence of non-translated sequences reduced gag expression (for example, the RRE sequence in p17R), suggests that translation of the inhibitory/instability region is not necessary for inhibition. Introduction of RRE and 3' HIV sequences in p17M1234 was also able to decrease gag expression, verifying that independent negative elements not acting co-translationally are responsible for poor expression.

To examine the effect of removal of INS in the p17$^{gag}$ coding region (the p17$^{gag}$ coding region spans nucleotides 336–731, as described in the description of FIG. 1. (B) above, and contains the first of three parts (i.e., p17, p24, and p15) of the gag coding region, as indicated on in FIGS. 1. (A) and (B)) on the expression of the complete gag gene expression vectors were constructed in which additional sequences of the gag gene were inserted 3' to the mutationally altered p17$^{gag}$ coding region, downstream of the stop codon, of vector p17M1234. Three vectors containing increasing lengths of gag sequences were studied: p17M1234(731–1081), p17M1234(731–1424) and p17M1234(731–2165), as shown in FIG. 1. (C). Levels of expression of p17$^{gag}$ were measured, with the results indicating that region of the mRNA encoding the second part of the gag protein (i.e., the part encoding the p24$^{gag}$ protein, which spans nucleotides 731–1424) contains only a weak INS, as determined by a small reduction in the amount of p17$^{gag}$ protein expressed by p17M1234 as compared with the amount of p17$^{gag}$ protein expressed by p17M1234 (731–1424), while the region of the mRNA encoding the third part of the gag protein (i.e., the part encoding the p15$^{gag}$ protein, which spans nucleotides 1425–2165) contains a strong INS, as determined by a large reduction in the amount of gag protein expressed by p17M1234(731–2165) as compared with the amount of protein expressed by p17M1234 and p17M1234(731–1424). This analysis allowed the construction of vector p37M1234, which expressed high levels of p37$^{gag}$ precursor protein (which contains both the p17 and p24 gag protein regions). Vector p37M1234 was constructed by removing the stop codon at the end of the gene encoding the altered p17$^{gag}$ protein and fusing the nucleotide sequence encoding the p24$^{gag}$ protein into the correct reading frame by oligonucleotide mutagenesis. This restored the nucleotide sequence so that it encoded the fused p17$^{gag}$ and p24$^{gag}$ protein (i.e., the p37$^{gag}$ protein) as it is encoded by HIV-1. Other vectors which were constructed in a similar manner as was P37M1234 were p17M1234(731–1081)NS and p55MB1234 (FIG. 1. (C)). The levels of gag expression from each of the three vectors was respectively similar to the level of gag expression from the expression from the vectors containing the nucleotide sequences 3' to the stop codon (i.e., vectors p17M1234 (731–1081), p17M1234(731–1424) and p17M1234 (731–2165), described above). These results also demonstrate that the INS regions in the gag gene are not affected by translation. These results demonstrate the use of p17M1234 to detect additional INS sequences in the HIV-1 gag coding region (i.e., in the 1424–2165 encoding region of HIV-1 gag). Thus, these results also demonstrate how a gene containing one or more inhibitory/instability regions can be mutated to eliminate one inhibitory/instability region and then used to further locate additional inhibitory/instability regions within that gene, if any. Since the presence of the p37$^{gag}$ protein can be quantitated easily by commercially available ELISA kits, vector p37M1234 can be used for inserting and testing additional fragments suspected of containing INS. Using these protocols, regions have been identified within the gp41 (the transmembrane part of HIV-1 env) coding area and at the post-env 3' region of HIV-1 which contain INS. The elimination of INS from gag and env regions will allow the expression of high levels of structural proteins in the absence of the Rev regulatory factor of HIV-1. The mutated coding sequences can be used for direct expression in human or other cells in vitro or in vivo with the goal being the production of high protein levels and the generation of a strong immune response.

The described experiments demonstrate that the inhibitory/instability sequences are required to prevent HIV-1 expression. This block to the expression of viral structural proteins can be overcome by the Rev-RRE interaction. In the absence of INS, HIV-1 expression would be similar to simpler retroviruses and would not require Rev. Thus, the INS is a necessary component of Rev regulation. Sequence comparisons suggest that the INS element identified here is conserved in all HIV-1 isolates, although this has not been verified experimentally. The majority (22 of 28) of the mutated nucleotides in gag are conserved in all HIV-1 isolates, while 22 of 28 are conserved also in HIV-2 (G. Myers, et al., Eds. *Human retroviruses and AIDS. A compilation and analysis of nucleic acid and amino acid sequences* (Los Alamos National Laboratory, Los Alamos, N. Mex., 1991), incorporated herein by reference). Several lines of evidence indicate that all lentiviruses and other complex retroviruses such as the HTLV group contain similar INS regulatory elements. Strong INS elements have been identified in the gag region of HTLV-I and SIV (manuscript in preparation). This suggests that INS are important regulatory elements, and may be responsible for some of the biological characteristics of the complex retroviruses. The presence of INS in SIV and HTLV-I suggests that these elements are conserved among complex retroviruses. Since INS inhibit expression, it must be concluded that their presence is advantageous to the virus, otherwise they would be rapidly eliminated by mutations.

The observations that the inhibitory/instability sequences act in the absence of any other viral proteins and that they can be inactivated by mutagenesis suggest that these elements may be targets for the binding of cellular factors that interact with the mRNA and inhibit post transcriptional steps of gene expression. The interaction of HIV-1 mRNAs with such factors may cause nuclear retention, resulting in either further splicing or rapid degradation of the mRNAs. It has been proposed that components of the splicing machinery interact with splice sites in HIV-1 mRNAs and modulated mRNA expression (A. Cochrane et al., J. Virol. 65:5305–5313 (1991); D. Chang and P. Sharp, Cell 59:789–795 (1989); X. Lu et al., Proc. Natl. Acad. Sci. USA 87:7598–7602 (1990)). However, it is not likely that the inhibitory/instability elements described here are functional 5' or 3' splice sites. Thorough mapping of HIV-1 splice sites performed by several laboratories using the Reverse Transcriptase-PCR technique failed to detect any splice sites within gag (S. Schwartz et al., J. Virol. 64:2519–2529 (1990); J. Guatelli et al., J. Virol. 64:4093–4098 (1990); E. D. Gerrett et al., J. Virol. 65:1653–1657 (1991); M. Robert-Guroff et al., J. Virol. 64:3391–3398 (1990); S. Schwartz et al., J. Virol. 64:5448–5456 (1990); S. Schwartz et al., Virology 183:677–686 (1991)). The suggestions that Rev may act by dissociating unspliced mRNA from the splicesomes (D. Chang and P. Sharp, Cell 59:789–795 (1989)) or by inhibiting splicing (J. Kjems et al., Cell 67:169–178 (1991)) are not easily reconciled with the knowledge that all retroviruses produce structural proteins from mRNAs that contain unutilized splice sites. Splicing of all retroviral mRNAs, including HIV-1 mRNAs in the absence of Rev, is inefficient compared to splicing of cellular mRNAs (J. Kjems et al., Cell 67:169–178 (1991); A. Krainer et al., Gene Dev. 4:1158–1171 (1990); R. Katz and A. Skalka, Mol. Cell. Biol. 10:696–704 (1990); C. Stoltzfus and S. Fogarty, J. Virol. 63:1669–1676 (1989)). The majority of the retroviruses do not produce Rev-like proteins, yet they efficiently express proteins from partially spliced mRNAs, suggesting that inhibition of expression by unutilized splice sites is not a general property of retroviruses. Experiments using constructs expressing mutated HIV-1 gag and env mRNAs lacking functional splice sites showed that only low levels of these mRNAs accumulated in the absence of Rev and that their expression was Rev-dependent (M. Emerman et al., Cell 57:1155–1165 (1989); B. Felber et al., Proc. Natl. Acad. Sci. USA 86:1495–1499 (1989); M. Malim et al., Nature (London) 338:254–257 (1989)). This led to the conclusion that Rev acts independently of splicing (B. Felber et al., Proc. Natl. Acad. Sci. USA 86:1495–1499 (1989); M. Malim et al., Nature (London) 338:254–257 (1989)) and to the proposal that inhibitory/instability elements other than splice sites are present on HIV-1 mRNAs (C. Rosen et al., Proc. Natl. Acad. Sci. USA 85:2071–2075 (1988); M. Hadzopoulou-Cladaras, et al., J. Virol. 63:1265–1274 (1989); B. Felber et al., Proc. Natl. Acad. Sci. USA 86:1495–1499 (1989)).

Construction of the Gag Expression Plasmids

Plasmid p17R has been described as pNL17R (S. Schwartz et al., J. Virol. 66:150–159 (1992)). Plasmid p17 was generated from p17R by digestion with Asp718 followed by teligation. This procedure deleted the RRE and HIV-1 sequences spanning nt 8021–8561 upstream of the 3' LTR. To generate mutants of p17$^{gag}$, the p17$^{gag}$ coding sequence was subcloned into a modified pBLUESCRIPT vector (Stratagene) and generated single stranded uracil-containing DNA. Site-directed mutagenesis was performed as described (T. Kunkel, Proc. Natl. Acad. Sci. USA 82:488–492 (1985); S. Schwartz et al., Mol. Cell Biol. 12:207–219 (1992)). Clones containing the appropriate mutations were selected by sequencing of double-stranded DNA. To generate plasmid p19R, plasmid p17R was first digested with BssHII and EcoRI, thereby deleting the entire p17$^{gag}$ coding sequence, six nucleotides upstream of the p17$^{gag}$ AUG and nine nucleotides of linker sequences 3' of the p17$^{gag}$ stop codon. The p17$^{gag}$ coding sequence in p17R was replaced by a PCR-amplified DNA fragment containing the RSV p19$^{gag}$ coding sequence (R. Weiss et al., RNA Tumor Viruses. Molecular Biology of Tumor Viruses (Cold Spring Harbor Laboratory, Cold Spring Harbor, N.Y., 1985)). This fragment contained eight nucleotides upstream of the RSV gag AUG and the p19$^{gag}$ coding sequence immediately followed by a translational stop, codon. The RSV gag fragment was derived form the infectious RSV proviral clone S-RA (R. Weiss et al., RNA Tumor Viruses. Molecular Biology of Tumor Viruses (Cold Spring Harbor Laboratory, Cold Spring Harbor, N.Y., 1985)). p19 was derived from p19R by excising an Asp 718 fragment containing the RRE and 3' HIV-1 sequences spanning nt 8021–8561.

Transfection of HLtat Cells With Gag Expression Plasmids

HLtat cells (S. Schwartz et al., J. Virol. 64:2519–2529 (1990)) were transfected using the calcium coprecipitation technique (F. Graham et al. and A. Van der Eb, Virology 52:456–460 (1973)) as described (B. Felber et al., Proc. Natl. Acad. Sci. USA 86:1495–1499 (1989)), using 5 μg of p17, p17R, p17M1234, p19, or p19R in the absence (-) or presence (+) of 2 μg of the Rev-expressing plasmid pL3crev (B. Felber et al., Proc. Natl. Acad. Sci. USA 86:1495–1499 (1989)). The total amount of DNA in transfections was adjusted to 17 μg per 0.5 ml of precipitate per 60 mm plate using pUC19 carrier DNA. Cells were harvested 20 h after transfected and cell extracts were subjected to electrophoresis on 12.5% denaturing polyacrylamide gels and analyzed by immunoblotting using either human HIV-1 patient serum (Scripps) or a rabbit anti-p19$^{gag}$ serum. pRSV-luciferase (J. de Wet et al., Mol. Cell. Biol. 7:725–737 (1987)) that contains the firefly luciferase gene linked to the RSV LTR promoter, was used as an internal standard to control for transfection efficiency and was quantitated as described (L. Solomin et al., J. Virol. 64:6010–6017 (1990)). The results are set forth in FIG. 2.

Northern Blot Analysis

HLtat cells were transfected as described above and harvested 20 h post transfection. Total RNA was prepared by the heparin/DNase method (Z. Krawczyk and C. Wu, Anal. Biochem. 165:20–27 (1987)), and 20 μg of total RNA was subjected to northern blot analysis as described (M. Hadzopoulou-Cladaras et al., J. Virol. 63:1265–1274 (1989)). The filters were hybridized to a nick-translated PCR-amplified DNA fragment spanning nt 8304–9008 in the HIV-1 3' LTR. The results are set forth in FIG. 3.

EXAMPLE 2

HIV-1 ENV GENE

Fragments of the env gene were inserted into vectors p19, p17M1234 or p37M1234 and the expression of the resulting plasmids were analyzed by transfections into HLtat cells. It was found that several fragments inhibited protein expression. One of the strong INS identified was in the fragment containing nucleotides 8206–8561 ("fragment [8210–8561]"). To eliminate this INS, the following oligonucleotides were synthesized and used in mutagenesis experiments as specified supra.

The oligonucleotides which were used to mutagenize fragment [8206–8561], and which made changes in the env coding region between nucleotides 8210–8555 (the letters in lower case indicate mutated nucleotides) were:

1:
8194–8261
G A A T A G T G C T G T T A A C c T c C T g A A c G C- tACcGCtATcGCcGTgGCgGAaGGaACcGAcAG GGTI- ATAG (SEQ ID NO.:10)

2
8262–8323
A A G T A T T A C A A G C c G C c T A c c G c G C c AT- caGaCAtATcCCccGccGcATccGcCAGGG CTTG (SEQ ID NO.: 11)

3
8335–8392
G C T A T A A G A T G G G c G G t A A a T G G a g- cAAgtcctccGTcATcGGcTGGCCTGCTGTAAG (SEQ ID NO.: 12)

4
8393–8450
G G A A A G A A T G c G c a G g G C c G A a C C c G C- cGCcGAcGGaGTtGGcGCcGTATCTCGAGAC (SEQ ID NO.:13)

5
8451–8512
C T A G A A A A A C A c G G c G C c A T t A C c t c- ctctAAcACcGCcGCcAAtAAcGCcGCTTGTG CCTG (SEQ ID NO.: 14)

6
8513–8572
G C T A G A A G C A C A g G A a G A a G A g- GAaGTcGGcTTcCCcGTtACcCCCTCAGGTACCTTTA AG (SEQ ID NO.: 15)

The expression of env was increased by the elimination of the INS in fragment [8206–8561] as determined by analysis of both mRNA and protein.

EXAMPLE 3

PROTO-ONCOGENE C-FOS

Fragments of the fos gene were inserted into the vector p19 and the expression of the resulting plasmids were analyzed by transfections into HLtat cells. It was found that several fragments inhibited protein expression. A strong INS was identified in the fragment containing nucleotides 3328–3450 ("fragment [3328–3450]") (nucleotides of the fos gene are numbered according to Genebank sequence entry HUMCFOT, ACCESSION # V01512). In addition, a weaker element was identified in the coding region.

To eliminate these INS the following oligonucleotides were synthesized and are used in mutagenesis experiments as specified supra.

To eliminate the INS in the fos non-coding region, the following oligonucleotides, which make changes in the fos non-coding region between nucleotides [3328–3450] (the letters in lower case indicate mutated nucleotides), were synthesized and are used to mutagenize fragment [3328–3450]: mutagenesis experiments as specified supra:

1:
3349–3391
T G A A A A C G T T c g c a T G T G T c g c T A c g T- TgcTTAcTAAGATGGA (SEQ ID NO.: 16)

2:
3392–3434
T T C T C A G A T A c c T A g c T T c a T A T T g c c T- TaTTgTCTACCTTGA (SEQ ID NO.: 17)

These oligonucleotides are used to mutagenize fos fragment [3328–3450] inserted into vectors p19, p17M1234 or p37M1234 and the expression of the resulting plasmids are analyzed after transfection into HLtat cells.

The expression of fos is expected to be increased by the elimination of this INS region.

To further define and eliminate the INS elements in the coding region, additional longer fragments of fos are introduced into vector p37M1234. The INS element in the coding region is first mapped more precisely using this expression vector and is then corrected using the following oligonucleotides:

1
2721–2770
G C C C T G T G A G t a G G C A c t G A A G G a c A G c- CAtaCGtaACatACAAGTGCCA (SEQ ID NO.: 18)

2
2670–2720
A G C A G C A G C A A T G A a C C T a g t a g c G A t- agcCTgAGtagcCCtACGCTGCTG (SEQ ID NO.: 19)

3
2620–2669
A C C C C G A G G C a G A t a g C T T t C C a t c c T- GcGCtGCcGCtCACCGCAAGGGC (SEQ ID NO.: 20)

4
2502–2562
C T G C A C A G T G G a a g C C T c G G a A T G G G c- CCtATGGCtACcGAatTGGAaCCaCTGTGCA CTC (SEQ ID NO.: 21)

The expression of fos is expected to be increased by the elimination of this INS region.

Those skilled in the art will recognize that any gene encoding a mRNA containing an inhibitory/instability sequence or sequences can be modified in accordance with the exemplified methods of this invention or their functional equivalents.

Modifications of the above described modes for carrying out the invention that are obvious to those of skill in the fields of genetic engineering, protein chemistry, medicine, and related fields are intended to be within the scope of the following claims.

Every reference cited hereinbefore is hereby incorporated by reference in its entirety.

TABLE 1

Correspondence between Sequence Identification Numbers and Nucleotides in FIG. 4

| Sequence ID Nos. | FIG. 4 |
| --- | --- |
| SEQ ID NO.:1 | nucleotides 336–731 |
| SEQ ID NO.:2 | nucleotides 402–452, above line |
| SEQ ID NO.:3 | nucleotides 536–583, above line |
| SEQ ID NO.:4 | nucleotides 585–634, above line |
| SEQ ID NO.:5 | nucleotides 654–703, above line |
| SEQ ID NO.:6 | nucleotides 402–452, below line (M1) |
| SEQ ID NO.:7 | nucleotides 536–583, below line (M2) |
| SEQ ID NO.:8 | nucleotides 585–634, below line (M3) |
| SEQ ID NO.:9 | nucleotides 654–703, below line (M4) |

What is claimed is:

1. A method for reducing the effect of inhibitory/instability sequences within the coding region of a mRNA, wherein said effect of said inhibitory/instability sequences is a post-transcriptional effect, said method comprising the steps of:
    (a) providing a gene which encodes said mRNA;
    (b) identifying the inhibitory/instability sequences within said gene which encode said inhibitory/instability sequences within the coding region of said mRNA;
    (c) mutating said inhibitory/instability sequences within said gene by making multiple point mutations;
    (d) transfecting said mutated gene into a cell;
    (e) culturing said cell in a manner to cause expression of said mutated gene;
    (f) detecting the level of expression of said gene to determine whether the effect of said inhibitory/instability sequences within the coding region of the mRNA has been reduced.

2. The method of claim 1 further comprising the step of fusing said mutated gene to a reporter gene prior to said transfecting step and said detecting step is performed by detecting the level of expression of said reporter gene.

3. The method of claim 1 wherein step (b) further comprises the steps of
    (a) fusing said gene or fragments of said gene to a reporter gene to create a fused gene;
    (b) transfecting said fused gene into a cell;
    (c) culturing said cell in a manner to cause expression of said fused gene;
    (d) detecting the level of expression of said fused gene to determine whether the expression of said fused gene is reduced relative to the expression of said reporter gene.

4. The method of claim 3 wherein step (a) comprises fusing said gene or fragments of said gene 3' to the stop codon of said reporter gene.

5. The method of claim 3 wherein step (a) comprises fusing said gene or fragments of said gene in frame with the 3' end of the coding region of said reporter gene.

6. The method of claim 1 or 2 wherein said mutating step changes the codons such that the amino acid sequence encoded by the mRNA is unchanged.

7. The method of claim 6 wherein said inhibitory/instability sequences are AT-rich and wherein said mutating step comprises substituting either G or C for either A or T and wherein the final nucleotide composition of said mutated inhibitory sequence is about 50% A and T and about 50% G and C.

8. The method of claim 6 wherein at least 75% of the point mutations replace conserved nucleotides with non-conserved nucleotides.

9. The method of claim 6 wherein said mutating step comprises substituting less preferred codons with more preferred codons.

10. The method of claim 1 or 2 wherein said mRNA encodes the GAG protein of a Rev-dependent complex retrovirus.

11. The method of claim 10 wherein the Rev-dependent complex retrovirus is human immunodeficiency virus-1.

* * * * *

UNITED STATES PATENT AND TRADEMARK OFFICE
CERTIFICATE OF CORRECTION

PATENT NO. : 6,174,666 B1
DATED : January 16, 2001
INVENTOR(S) : George N. Pavlakis and Barbara K. Felber It is certified that error appears in the above-identified patent and that said Letters Patent is hereby corrected as shown below:

<u>Title page,</u>
Item [56], References Cited, and before "FOREIGN PATENT DOCUMENTS", insert --    U.S. PATENT DOCUMENTS

| | | | |
|---|---|---|---|
| RE 33,653 | 7/30/91 | Mark et al. | 424/85.1 |
| 5,073,627 | 12/17/91 | Curtis et al. | 530/351 |
| 5,082,767 | 1/21/92 | Hatfield et al. | 435/6. -- |

FOREIGN PATENT DOCUMENTS, replace " WO9011902" with -- WO9011092 --.

OTHER PUBLICATIONS, insert the following references:

-- B.A. Bunnell et al., "A Dominant Negative Mutation in Two Proteins Created by Ectopic Expression of an AuRich 3' Untranslated Region", *Somataic Cell and Mol. Genet.* <u>16</u>:151-162 (1990)

D. Caput et al., "Identification of a common nucleotide sequence in the 3'-untranslated region of mRNA molecules specifying inflammatory mediators", *Proc. Natl. Acad. Sci.* <u>83</u>:1670-1674 (1986)

P. Carter-Muenchau and R. Wolf, "Growth-rate-dependent regulation of 6-phosphogluconate dehydrogenase level mediated by an anti-Shine-Dalgarno sequence located within the <u>Escherichia</u> <u>coli</u> <u>gnd</u> structural gene", *Proc. Natl. Acad. Sci., USA,* <u>86</u>:1138-1142 (1989)

A.W. Cochrane et al., "Identification and Characterization of Intragenic Sequences Which Repress Human Immunodeficiency Virus Structural Gene Expression", *J. Virol.* <u>65</u>:5303-5313 (1991)

M.D. Cole and S.E. Mango, "<u>cis</u>-Acting Determinants of c-<u>myc</u> mRNA Stability, *Enzyme* <u>44</u>:167-180 (1990)

M.D. Edge et al. "Total Synthesis of a Human Leukocyte Interferon Gene", *Nature* <u>292</u>:756-762 (1981)

UNITED STATES PATENT AND TRADEMARK OFFICE
CERTIFICATE OF CORRECTION

PATENT NO.    : 6,174,666 B1
DATED         : January 16, 2001
INVENTOR(S)   : George N. Pavlakis and Barbara K. Felber It is certified that error appears in the above-identified patent and that said Letters Patent is hereby corrected as shown below:

M. Emerman, "The rev Gene Product of the Human Immunodeficiency Virus Affects Envelope-Specific RNA Localization", *Cell* 57:1155-1165 (1989)

B. Felber et al., "rev protein of human immunodeficiency virus type 1 affects the stability and transport of the viral mRNA", *Proc. Natl. Acad. Sci. USA* 86:1495-1499 (1989)

M. Hadzopoulou-Cladaras et al., "The rev (trs/art) Protein of Human Immunodeficiency Virus Type 1 Affects Viral mRNA and Protein Expression via a cis-Acting Sequence in the env Region", *J. Virol.* 63:1265-1274 (1989)

M.W. Hentze, "Determinants and regulation of cytoplasmic mRNA stability in eukaryotic cells", *Biochem. Biophys. Acta* 1090: 281-292 (1991)

E. Jay et al., "Chemical Synthesis of a Biologically Active Gene for Human Immune Interferon-$\gamma$", *J. Biol. Chem.* 259:6311-6317 (1984)

T. R. Jones and M.D. Cole, "Rapid Cytoplasmic Turnover of c-myc mRNA: Requirement of the 3' Untranslated Sequences", *Mol. Cell Biol.* 7:4513-4521 (1987)

R. Kamen et al., "A Novel Mechanism of Post Transcriptional, Sequence-Specific Regulation of mRNA Stability", *J. Cell Bio.* Supp. 10D (1986):152 (Abst. No. 0210)

D.M. Koeller et al., "Translation and the stability of mRNAs encoding the transferrin receptor and c-fos", *Proc. Natl. Acad. Sci. USA* 88:7778-7782 (1991)

V. Kruys et al., "Constitutive activity of the tumor necrosis factor promoter is canceled by the 3' untranslated region in nonmacrophage cell lines; a trans-dominant factor overcomes this suppressive effect", *Proc. Natl. Acad. Sci. USA* 89:673-677(1992)

UNITED STATES PATENT AND TRADEMARK OFFICE
CERTIFICATE OF CORRECTION

PATENT NO. : 6,174,666 B1
DATED : January 16, 2001
INVENTOR(S) : George N. Pavlakis and Barbara K. Felber It is certified that error appears in the above-identified patent and that said Letters Patent is hereby corrected as shown below:

T.A. Kunkel, "Rapid and efficient site-specific mutagenesis without phenotypic selection", *Proc. Natl. Acad. Sci. USA* 82:488-492 (1985)

I.A. Laird-Offringa et al., "Rapid c-myc mRNA degradation does not require (A+U)- rich sequences or complete translation of the mRNA", *Nucleic Acids Res.* 19:2387-2394 (1991)

M.D. Lundigran et al., "Transcribed sequences of the Escherichia coli btuB gene control its expression and regulation by vitamin $B_{12}$", *Proc. Natl. Acad. Sci. USA* 88:1479-1483 (1991)

F. Maldarelli et al., "Identification of Posttranscriptionally Active Inhibitory Sequences in Human Immunodeficiency Virus Type 1 RNA: Novel Level of Gene Regulation", *J. Virol.* 65:5732-5743 (1991)

K.P. Nambiar et al., "Total synthesis and Cloning of a Gene Coding for the Ribonuclease S Protein", Science 223:1299-1301(1984)

R. Parker and A. Jacobson, "Translation and a 42-nucleotide segment within the coding region of the mRNA encoded by the MATα 1 gene are involved in promoting rapid mRNA decay in yeast", *Proc. Natl. Acad. Sci. USA* 87:2780-2784 (1990)

C.A. Rosen, "Intragenic cis-acting art gene-responsive sequences of the human immunodeficiency virus", *Proc. Natl. Acad. Sci., USA* 85:2071-2075 (1988)

S. Schwartz et al., "Distinct RNA Sequences in the gag region of Human Immunodeficiency Virus Type 1 Decrease RNA Stability and Inhibit Expression in the Absence of Rev Protein", *J. Virol.* 66:150-159 (1992)

G. Shaw and R. Kamen, "A Conserved AU Sequence from the 3' Untranslated Region of GM-CSF mRNA Mediates Selective mRNA Degradation", Cell 46:659-667 (1986)

UNITED STATES PATENT AND TRADEMARK OFFICE
CERTIFICATE OF CORRECTION

PATENT NO. : 6,174,666 B1
DATED : January 16, 2001
INVENTOR(S) : George N. Pavlakis and Barbara K. Felber It is certified that error appears in the above-identified patent and that said Letters Patent is hereby corrected as shown below:

G. Shaw and R. Kamen, "A Conserved AU Sequence from the 3' Untranslated Region of GM-CSF mRNA Mediates Selective mRNA Degradation", *J. Cell. Bio.* Supp. 11 C (1987):132 (Abst. No. L541)

A.-B. Shyu et al., "Two distinct destabilizing elements in the c-fos message trigger deadenylation as a first step in rapid mRNA decay", *Gen. & Devel.* 5:221-231 (1991)

C.M. Stoltzfus and S.J. Fogarty, "Multiple Regions in the Rous Sarcoma Virus src Gene Intron Act in cis To Affect the Accumulation of Unspliced RNA", *J. Virol.* 63:1669-1676 (1989)

T. Wilson and R. Treisman, "Removal of poly(A) and consequent degradation of c-fos mRNA facilitated by 3' AU-rich sequences", *Nature* 336:396-399 (1988)

R. Wisdom and W. Lee, "The protein-coding region of c-myc mRNA contains a sequence that specifies rapid mRNA turnover and induction by protein synthesis inhibitors", *Gen. & Devel.* 5:232-243 (1991)

D.H. Wreschner and G. Rechavi, "Differential mRNA stability to reticulocyte ribonucleases correlates with 3' noncoding $(U)_nA$ sequences", *Eur. J. Biochem.* 172:333-340 (1988). --

Signed and Sealed this

Eighteenth Day of March, 2003

JAMES E. ROGAN
*Director of the United States Patent and Trademark Office*

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
       (A) LENGTH: 396
       (B) TYPE: NUCLEIC ACID
       (C) STRANDEDNESS: SINGLE
       (D) TOPOLOGY: UNKNOWN (ii) MOLECULE TYPE: RNA (iii) HYPOTHETICAL: NO (vi) ORIGINAL SOURCE:
       (A) ORGANISM: HIV-1
       (B) STRAIN:
       (C) INDIVIDUAL ISOLATE:
       (D) DEVELOPMENTAL STAGE:
       (E) HAPLOTYPE:
       (F) TISSUE TYPE:
       (G) CELL TYPE:
       (H) CELL LINE:
       (I) ORGANELLE:

(ix) FEATURE:
       (A) NAME/KEY:
       (B) LOCATION:
       (C) IDENTIFICATION METHOD:
       (D) OTHER INFORMATION: THE P17 GAG CODING
           SEQUENCE SPANNING NT 336-731 OF THE
           REVISED NUCLEOTIDE SEQUENCE OF THE HIV-1
           MOLECULAR CLONE PHXB2

(xi) SEQUENCE DESCRIPTION:SEQ ID NO: 1:

ATGGGTGCGA GAGCGTCAGT ATTAAGCGGG GGAGAATTAG ATCGATGGGA AAAAATTCGG    60

TTAAGGCCAG GGGGAAAGAA AAAATATAAA TTAAAACATA TAGTATGGGC AAGCAGGGAG   120

CTAGAACGAT TCGCAGTTAA TCCTGGCCTG TTAGAAACAT CAGAAGGCTG TAGACAAATA   180

CTGGGACAGC TACAACCATC CCTTCAGACA GGATCAGAAG AACTTAGATC ATTATATAAT   240

ACAGTAGCAA CCCTCTATTG TGTGCATCAA AGGATAGAGA TAAAAGACAC CAAGGAAGCT   300

TTAGACAAGA TAGAGGAAGA GCAAAACAAA AGTAAGAAAA AAGCACAGCA AGCAGCAGCT   360

GACACAGGAC ACAGCAATCA GGTCAGCCAA AATTAC                            396

(2) INFORMATION FOR SEQ ID NO: 2:

(i) SEQUENCE CHARACTERISTICS:
       (A) LENGTH: 51
       (B) TYPE: NUCLEIC ACID
       (C) STRANDEDNESS: SINGLE
       (D) TOPOLOGY: UNKNOWN (ii) MOLECULE TYPE: RNA (iii) HYPOTHETICAL: NO (vi) ORIGINAL SOURCE:
       (A) ORGANISM: HIV-1
       (B) STRAIN:
       (C) INDIVIDUAL ISOLATE:
       (D) DEVELOPMENTAL STAGE:
       (E) HAPLOTYPE:
       (F) TISSUE TYPE:
       (G) CELL TYPE:
       (H) CELL LINE:
       (I) ORGANELLE:

(ix) FEATURE:
            (A) NAME/KEY:
            (B) LOCATION:
            (C) IDENTIFICATION METHOD:
            (D) OTHER INFORMATION:  CODING SEQUENCE SPANNING NT
                  402-452 OF THE REVISED NT SEQUENCE OF THE HIV-1
                  MOLECULAR CLONE PHXB2

(xi) SEQUENCE DESCRIPTION:SEQ ID NO: 2:

CCAGGGGGAA AGAAAAAATA TAAATTAAAA CATATAGTAT GGGCAAGCAG G            51

(2) INFORMATION FOR SEQ ID NO: 3:

(i) SEQUENCE CHARACTERISTICS:
            (A) LENGTH:  48
            (B) TYPE:  NUCLEIC ACID
            (C) STRANDEDNESS:  SINGLE
            (D) TOPOLOGY:  UNKNOWN (ii) MOLECULE TYPE:  RNA (iii) HYPOTHETICAL:  NO (vi) ORIGINAL SOURCE:
            (A) ORGANISM:  HIV-1
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(ix) FEATURE:
            (A) NAME/KEY:
            (B) LOCATION:
            (C) IDENTIFICATION METHOD:
            (D) OTHER INFORMATION:  CODING SEQUENCE SPANNING NT
                  536-583 OF THE REVISED NT SEQUENCE OF THE HIV-1
                  MOLECULAR CLONE PHXB2

(xi) SEQUENCE DESCRIPTION:SEQ ID NO: 3:

CCTTCAGACA GGATCAGAAG AACTTAGATC ATTATATAAT ACAGTAGC               48

(2) INFORMATION FOR SEQ ID NO: 4:

(i) SEQUENCE CHARACTERISTICS:
            (A) LENGTH:  50
            (B) TYPE:  NUCLEIC ACID
            (C) STRANDEDNESS:  SINGLE
            (D) TOPOLOGY:  UNKNOWN (ii) MOLECULE TYPE:  RNA (iii) HYPOTHETICAL:  NO (vi) ORIGINAL SOURCE:
            (A) ORGANISM:  HIV-1
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(ix) FEATURE:
            (A) NAME/KEY:
            (B) LOCATION:
            (C) IDENTIFICATION METHOD:
            (D) OTHER INFORMATION:  CODING SEQUENCE SPANNING NT
                  585-634 OF THE REVISED NT SEQUENCE OF THE HIV-1

MOLECULAR CLONE PHXB2

(xi) SEQUENCE DESCRIPTION:SEQ ID NO: 4:

ACCCTCTATT GTGTGCATCA AAGGATAGAG ATAAAAGACA CCAAGGAAGC          50

(2) INFORMATION FOR SEQ ID NO: 5:

(i) SEQUENCE CHARACTERISTICS:
        (A) LENGTH: 50
        (B) TYPE: NUCLEIC ACID
        (C) STRANDEDNESS: SINGLE
        (D) TOPOLOGY: UNKNOWN (ii) MOLECULE TYPE: RNA (iii) HYPOTHETICAL: NO (vi) ORIGINAL SOURCE:
        (A) ORGANISM: HIV-1
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(ix) FEATURE:
        (A) NAME/KEY:
        (B) LOCATION:
        (C) IDENTIFICATION METHOD:
        (D) OTHER INFORMATION: CODING SEQUENCE SPANNING NT
            654-703 OF THE REVISED NT SEQUENCE OF THE HIV-1
            MOLECULAR CLONE PHXB2

(xi) SEQUENCE DESCRIPTION:SEQ ID NO: 5:

GAGCAAAACA AAAGTAAGAA AAAAGCACAG CAAGCAGCAG CTGACACAGG          50

(2) INFORMATION FOR SEQ ID NO: 6:

(i) SEQUENCE CHARACTERISTICS:
        (A) LENGTH: 51
        (B) TYPE: NUCLEIC ACID
        (C) STRANDEDNESS: SINGLE
        (D) TOPOLOGY: UNKNOWN (ii) MOLECULE TYPE: OTHER (iii) HYPOTHETICAL: YES (ix) FEATURE:
        (A) NAME/KEY:
        (B) LOCATION:
        (C) IDENTIFICATION METHOD:
        (D) OTHER INFORMATION: OLIGONUCLEOTIDE M1

(xi) SEQUENCE DESCRIPTION: SEQ ID NO: 6:

CCAGGGGGAA AGAAGAAGTA CAAGCTAAAG CACATCGTAT GGGCAAGCAG G        51

(2) INFORMATION FOR SEQ ID NO: 7:

(i) SEQUENCE CHARACTERISTICS:
        (A) LENGTH: 48
        (B) TYPE: NUCLEIC ACID
        (C) STRANDEDNESS: SINGLE
        (D) TOPOLOGY: UNKNOWN (ii) MOLECULE TYPE: OTHER (iii) HYPOTHETICAL: YES (ix) FEATURE:

```
        (A) NAME/KEY:
        (B) LOCATION:
        (C) IDENTIFICATION METHOD:
        (D) OTHER INFORMATION:  OLIGONUCLEOTIDE M2

(xi) SEQUENCE DESCRIPTION: SEQ ID NO: 7:

CCTTCAGACA GGATCAGAGG AGCTTCGATC ACTATACAAC ACAGTAGC                48

(2) INFORMATION FOR SEQ ID NO: 8:

(i) SEQUENCE CHARACTERISTICS:
        (A) LENGTH:  50
        (B) TYPE:  NUCLEIC ACID
        (C) STRANDEDNESS:  SINGLE
        (D) TOPOLOGY:  UNKNOWN (ii) MOLECULE TYPE:  OTHER (iii) HYPOTHETICAL:  YES (ix) FEATURE:
        (A) NAME/KEY:
        (B) LOCATION:
        (C) IDENTIFICATION METHOD:
        (D) OTHER INFORMATION:  OLIGONUCLEOTIDE M3

(xi) SEQUENCE DESCRIPTION:  SEQ ID NO: 8:

ACCCTCTATT GTGTGCACCA GCGGATCGAG ATCAAGGACA CCAAGGAAGC              50

(2) INFORMATION FOR SEQ ID NO: 9:

(i) SEQUENCE CHARACTERISTICS:
        (A) LENGTH:  50
        (B) TYPE:  NUCLEIC ACID
        (C) STRANDEDNESS:  SINGLE
        (D) TOPOLOGY:  UNKNOWN (ii) MOLECULE TYPE:  OTHER (iii) HYPOTHETICAL:  YES (ix) FEATURE:
        (A) NAME/KEY:
        (B) LOCATION:
        (C) IDENTIFICATION METHOD:
        (D) OTHER INFORMATION:  OLIGONUCLEOTIDE M4

(xi) SEQUENCE DESCRIPTION:  SEQ ID NO: 9:

GAGCAAAACA AGTCCAAGAA GAAGGCCCAG CAGGCAGCAG CTGACACAGG              50

(2) INFORMATION FOR SEQ ID NO: 10:

(i) SEQUENCE CHARACTERISTICS:
        (A) LENGTH:  68
        (B) TYPE:  NUCLEIC ACID
        (C) STRANDEDNESS:  SINGLE
        (D) TOPOLOGY:  UNKNOWN (ii) MOLECULE TYPE:  OTHER (iii) HYPOTHETICAL:  YES (ix) FEATURE:
        (A) NAME/KEY:
        (B) LOCATION:
        (C) IDENTIFICATION METHOD:
        (D) OTHER INFORMATION:  OLIGONUCLEOTIDE FOR MUTATING NT
            8194-8261 OF ENV GENE OF HIV-1 CLONE PNL43
            FOLLOWING

```
GGTTATAG                                                              68

(2) INFORMATION FOR SEQ ID NO: 11:

(i) SEQUENCE CHARACTERISTICS:
        (A) LENGTH: 62
        (B) TYPE: NUCLEIC ACID
        (C) STRANDEDNESS: SINGLE
        (D) TOPOLOGY: UNKNOWN (ii) MOLECULE TYPE: OTHER (iii) HYPOTHETICAL: YES (ix) FEATURE:
        (A) NAME/KEY:
        (B) LOCATION:
        (C) IDENTIFICATION METHOD:
        (D) OTHER INFORMATION: OLIGONUCLEOTIDE FOR MUTATING NT
              8262-8323 OF ENV GENE OF HIV-1 CLONE PNL43
              FOLLOWING THE NUMBERING SYSTEM OF CLONE PHXB2

(xi) SEQUENCE DESCRIPTION: SEQ ID NO: 11:

AAG (2) INFORMATION FOR SEQ ID NO: 14:

(i) SEQUENCE CHARACTERISTICS:
        (A) LENGTH: 62
        (B) TYPE: NUCLEIC ACID
        (C) STRANDEDNESS: SINGLE
        (D) TOPOLOGY: UNKNOWN (ii) MOLECULE TYPE: OTHER (iii) HYPOTHETICAL: YES (ix) FEATURE:
        (A) NAME/KEY:
        (B) LOCATION:
        (C) IDENTIFICATION METHOD:
        (D) OTHER INFORMATION: OLIGONUCLEOTIDE FOR MUTATING NT
            8451-8512 OF ENV GENE OF HIV-1 CLONE PNL43
            FOLLOWING THE NUMBERING SYSTEM OF CLONE PHXB2

(xi) SEQUENCE DESCRIPTION: SEQ ID NO: 14:

```
CTAGAAAAAC ACGGCGCCAT TACCTCCTCT AACACCGCCG CCAATAACGC CGCTTGTGCC    60

TG                                                                  62
```

(2) INFORMATION FOR SEQ ID NO: 15:

(i) SEQUENCE CHARACTERISTICS:
        (A) LENGTH: 60
        (B) TYPE: NUCLEIC ACID
        (C) STRANDEDNESS: SINGLE
        (D) TOPOLOGY: UNKNOWN (ii) MOLECULE TYPE: OTHER (iii) HYPOTHETICAL: YES (ix) FEATURE:
        (A) NAME/KEY:
        (B) LOCATION:
        (C) IDENTIFICATION METHOD:
        (D) OTHER INFORMATION: OLIGONUCLEOTIDE FOR MUTATING NT
            8513-8572 OF ENV GENE OF HIV-1 CLONE PNL43
            FOLLOWING THE NUMBERING SYSTEM OF CLONE PHXB2

(xi) SEQUENCE DESCRIPTION: SEQ ID NO: 15:

```
GCTAGAAGCA CAGGAAGAAG AGGAAGTCGG CTTCCCCGTT ACCCCTCAGG TACCTTTAAG    60
```

(2) INFORMATION FOR SEQ ID NO: 16:

(i) SEQUENCE CHARACTERISTICS:
        (A) LENGTH: 43
        (B) TYPE: NUCLEIC ACID
        (C) STRANDEDNESS: SINGLE
        (D) TOPOLOGY: UNKNOWN (ii) MOLECULE TYPE: OTHER (iii) HYPOTHETICAL: YES (ix) FEATURE:
        (A) NAME/KEY:
        (B) LOCATION:
        (C) IDENTIFICATION METHOD:
        (D) OTHER INFORMATION: OLIGONUCLEOTIDE FOR MUTATING NT
            3349-3391 OF C-FOS, HUMCFOT, ACC #V01512

(xi) SEQUENCE DESCRIPTION: SEQ ID NO: 16:

```
TGAAAACGTT CGCATGTGTC GCTACGTTGC TTACTAAGAT GGA                     43
```

(2) INFORMATION FOR SEQ ID NO: 17:

(i) SEQUENCE CHARACTERISTICS:
    (A) LENGTH: 43
    (B) TYPE: NUCLEIC ACID
    (C) STRANDEDNESS: SINGLE
    (D) TOPOLOGY: UNKNOWN (ii) MOLECULE TYPE: OTHER (iii) HYPOTHETICAL: YES (ix) FEATURE:
    (A) NAME/KEY:
    (B) LOCATION:
    (C) IDENTIFICATION METHOD:
    (D) OTHER INFORMATION: OLIGONUCLEOTIDE FOR MUTATING NT
        3392-3434 OF C-FOS, HUMCFOT, ACC #V01512

(xi) SEQUENCE DESCRIPTION: SEQ ID NO: 17:

TTCTCAGATA CCTAGCTTCA TATTGCCTTA TTGTCTACCT TGA                              43

(2) INFORMATION FOR SEQ ID NO: 18:

(i) SEQUENCE CHARACTERISTICS:
        (A) LENGTH: 50
        (B) TYPE: NUCLEIC ACID
        (C) STRANDEDNESS: SINGLE
        (D) TOPOLOGY: UNKNOWN (ii) MOLECULE TYPE: OTHER (iii) HYPOTHETICAL: YES (ix) FEATURE:
        (A) NAME/KEY:
        (B) LOCATION:
        (C) IDENTIFICATION METHOD:
        (D) OTHER INFORMATION: OLIGONUCLEOTIDE FOR MUTATING NT
            2721-2770 OF C-FOS, HUMCFOT, ACC #V01512

(xi) SEQUENCE DESCRIPTION: SEQ ID NO: 18:

GCCCTGTGAG TAGGCACTGA AGGACAGCCA TACGTAACAT ACAAGTGCCA                       50

(2) INFORMATION FOR SEQ ID NO: 19:

(i) SEQUENCE CHARACTERISTICS:
        (A) LENGTH: 51
        (B) TYPE: NUCLEIC ACID
        (C) STRANDEDNESS: SINGLE
        (D) TOPOLOGY: UNKNOWN (ii) MOLECULE TYPE: OTHER (iii) HYPOTHETICAL: YES (ix) FEATURE:
        (A) NAME/KEY:
        (B) LOCATION:
        (C) IDENTIFICATION METHOD:
        (D) OTHER INFORMATION: OLIGONUCLEOTIDE MUTATING NT
            2670-2720 OF C-FOS, HUMCFOT, ACC #V01512

(xi) SEQUENCE DESCRIPTION: SEQ ID NO: 19:

AGCAGCAGCA ATGAACCTAG TAGCGATAGC CTGAGTAGCC CTACGCTGCT G                     51

(2) INFORMATION FOR SEQ ID NO: 20:

(i) SEQUENCE CHARACTERISTICS:
        (A) LENGTH: 50
        (B) TYPE: NUCLEIC ACID
        (C) STRANDEDNESS: SINGLE
        (D) TOPOLOGY: UNKNOWN

-continued

```
    (ii) MOLECULE TYPE:  OTHER (iii) HYPOTHETICAL:  YES (ix) FEATURE:
         (A) NAME/KEY:
         (B) LOCATION:
         (C) IDENTIFICATION METHOD:
         (D) OTHER INFORMATION:  OLIGONUCLEOTIDE FOR MUTATING NT
             2620-2669 OF C-FOS, HUMCFOT, ACC #V01512

(xi) SEQUENCE DESCRIPTION:  SEQ ID NO: 20:

ACCCCGAGGC AGATAGCTTT CCATCCTGCG CTGCCGCTCA CCGCAAGGGC              50

(2) INFORMATION FOR SEQ ID NO: 21:

(i) SEQUENCE CHARACTERISTICS:
        (A) LENGTH:  61
        (B) TYPE:  NUCLEIC ACID
        (C) STRANDEDNESS:  SINGLE
        (D) TOPOLOGY:  UNKNOWN (ii) MOLECULE TYPE:  OTHER (iii) HYPOTHETICAL:  YES (ix) FEATURE:
         (A) NAME/KEY:
         (B) LOCATION:
         (C) IDENTIFICATION METHOD:
         (D) OTHER INFORMATION:  OLIGONUCLEOTIDE FOR MUTATING NT
             2502-2562 OF C-FOS, HUMCFOT, ACC #V01512

(xi) SEQUENCE DESCRIPTION:  SEQ ID NO: 21:

CTGCACAGTG GAAGCCTCGG AATGGGCCCT ATGGCTACCG AATTGGAACC ACTGTGCACT   60

C                                                                  61
```